United States Patent [19]

Lombardo

[11] Patent Number: 5,459,151
[45] Date of Patent: Oct. 17, 1995

[54] N-ACYL SUBSTITUTED PHENYL PIPERIDINES AS BRONCHODILATORS AND ANTIINFLAMMATORY AGENTS

[75] Inventor: Louis J. Lombardo, Somerset, N.J.

[73] Assignee: American Home Products Corporation, Madison, N.J.

[21] Appl. No.: 230,271

[22] Filed: Apr. 20, 1994

Related U.S. Application Data

[63] Continuation-in-part of Ser. No. 55,646, Apr. 30, 1993, abandoned.
[51] Int. Cl.⁶ .................. A61K 31/445; C07D 211/06; C07D 211/36
[52] U.S. Cl. .................. 514/318; 514/330; 546/194; 546/226
[58] Field of Search .................. 546/194, 226; 514/318, 330

[56] References Cited

U.S. PATENT DOCUMENTS

| | | | |
|---|---|---|---|
| 3,823,006 | 7/1974 | Lorenz | 71/94 |
| 4,198,417 | 4/1980 | Ong | 424/267 |
| 4,507,292 | 3/1985 | Heywang | 514/283 |
| 4,895,841 | 1/1990 | Sugimoto | 514/212 |
| 4,968,705 | 11/1990 | Regnier | 546/201 |

FOREIGN PATENT DOCUMENTS

| | | | |
|---|---|---|---|
| 0318029 | 11/1988 | European Pat. Off. | C07D 211/14 |
| 1812417 | 12/1968 | Germany | 546/226 |
| 561320 | 10/1957 | Netherlands | 546/194 |

OTHER PUBLICATIONS

Torphy et al., Molecular Pharmacology 37:206–214 (1990).
Thompson et al., Advances in Cyclic Nucleotide Research 10 (1979).
De and Ghose, J. Indian Chemical Society, 53(11), 1122–1125 (1976).
Nacci et al., Farmaco. Ed. Sci., 328(5), 399–410 (1973).

*Primary Examiner*—Ceila Chang
*Attorney, Agent, or Firm*—R. F. Boswell, Jr.

[57] ABSTRACT

This invention relates to novel PDE-IV inhibitors having the formula:

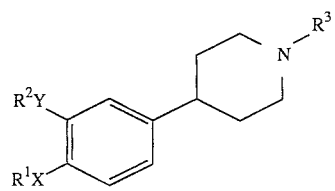

where:

$R^1$=H, $C_1$–$C_6$ alkyl;

$R^2$=$C_3$–$C_7$ alkyl, $C_3$–$C_7$ cycloalkyl or $C_4$–$C_8$ cycloalkylidene when Y is CH;

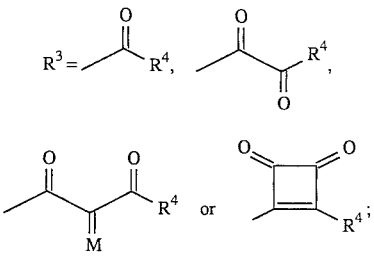

$R^4$=H, $OR^5$, $NHR^5$, NHOH, $NHNH_2$ or

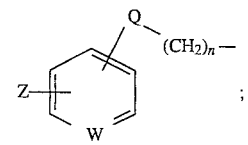

$R^5$=H, $C_1$–$C_6$ alkyl, $C_3$–$C_8$ cycloalkyl, aryl, substituted aryl, aralkyl, substituted aralkyl or

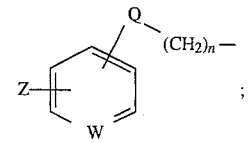

W=N or CH;

X=$CH_2$, O, S, or NH;

Y=$CH_2$, CH, O, S, or NH;

Q=a bond or CH=CH;

n=0, 1, 2, 3 or 4;

M=O, NOH or $H_2$;

Z=H or halogen;

or a pharmaceutically acceptable salt thereof, as antiasthmatic agents.

13 Claims, No Drawings

N-ACYL SUBSTITUTED PHENYL PIPERIDINES AS BRONCHODILATORS AND ANTIINFLAMMATORY AGENTS

This application is a continuation in part of application Ser. No. 08/055,646 filed on Apr. 30, 1993, abandoned.

This invention relates to novel phenyl pyrazolidinones having bronchodilator and antiinflammatory activity and being useful in the treatment of asthma.

Asthma is a disease in which respiratory distress is produced as a result of airway narrowing. This narrowing is caused largely by 1) the acute constriction of the respiratory smooth muscle that surrounds the airways and 2) chronic inflammation within the lung. Reversal of bronchospasm and prevention of pulmonary inflammation, then, are critical approaches to the relief of the symptoms of asthma.

One approach for reversing bronchospasm and also inhibiting inflammation is to elevate intracellular adenosine cyclic 3',5'-monophosphate (cAMP) in respiratory smooth muscle and inflammatory cells, respectively. The compound adenosine cyclic 3',5'-monophosphate is defined as a "second messenger" because it mediates a variety of effects performed by hormones, which are "first messengers." One of the more important roles is in mediating bronchodilation [see Sutherland et al., *Circulation*, 37, 279 (1968)]. The enzymatic mechanism for the inactivation of cyclic AMP has been known for some time [see Butcher et al., *Pharmacologist*, 1, 63 (1959)] and the enzyme responsible for this inactivation was identified a a magnesium dependent phosphodiesterase. The latter is capable of hydrolyzing cyclic AMP to adenosine monophosphate. Subsequent research has established that the xanthine-based bronchodilators, such as theophylline and aminophylline, mediate their bronchodilating activity via inhibition of cyclic AMP phosphodiesterase (PDE) [see *Lancet* 1970, 1119]. Agents that elevate smooth muscle cAMP concentrations induce rapid bronchodilation and inhibit the release of inflammatory mediators from activated leukocytes [see Hardman, in *Smooth Muscle, An Assessment of Current Knowledge*, Univ. of Texas Press, (1981); and Nielson et al., *American Review of Respiratory Disease*, 137, 25 (1988)]. By virtue of their dual mechanisms of action, such compounds can function as highly effective anti-asthmatic drugs.

Cyclic AMP concentrations within the living cell are determined by both the rate of its synthesis by adenylate cyclase and the rate of its degradation by phosphodiesterases. Thus, either stimulating adenylate cyclase or inhibiting PDEs in pulmonary tissues can result in anti-asthmatic activities. The most effective anti-asthmatic drugs are those which demonstrate the ability to inhibit a specific PDE, often called PDE IV, that selectively metabolizes cAMP and that is insensitive to the modulatory effects of guanosine cyclic 3',5'-monophosphate (cGMP) and calcium. This PDE is found in both respiratory smooth muscle and inflammatory cells, and has been demonstrated to be a principle regulator of cAMP in these tissues [see Torphy and Cieslinski, *Molecular Pharmacology*, 37, 206 (1990), and Dent, et al., *British Journal of Pharmacology*, 90, 163P (1990)]. Moreover, a variety of phosphodiesterase isozymes have been isolated from bronchial smooth muscles [see Silver et al., *Eur. J. Pharmacol.*, 150, 85 (1988)] and their kinetics have been studied using a variety of inhibitors. Consequently, the compounds named in this invention are both bronchodilatory and antiinflammatory, and are effective in animal models of allergic and non-allergic asthma. However, because the compounds named in this invention preferentially inhibit the PDE-IV isozyme, they are expected to be more selective and safer asthmatics than nonselective PDE inhibitors currently used for the treatment of asthma such as theophylline.

SUMMARY OF THE INVENTION

This invention provides novel PDE-IV inhibiting compounds of the general formula:

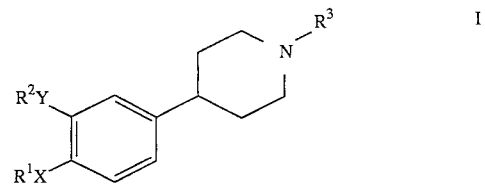

where:

$R^1$=H, $C_1$–$C_6$ alkyl;

$R^2$=$C_3$–$C_7$ alkyl, $C_3$–$C_7$ cycloalkyl or $C_4$–$C_8$ cycloalkylidene when Y is CH;

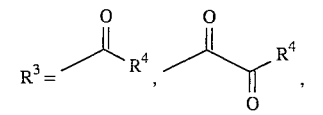

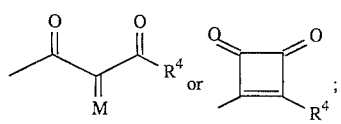

$R^4$=H, $OR^5$, $NHR^5$, NHOH, $NHNH_2$ or

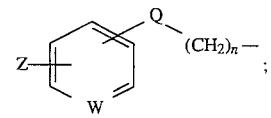

$R^5$=H, $C_1$–$C_6$ alkyl, $C_3$–$C_8$ cycloalkyl, aryl, substituted aryl, aralkyl, substituted aralkyl or

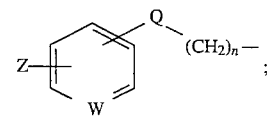

W=N or CH;

X=$CH_2$, O, S, or NH;

Y=$CH_2$, CH, O, S, or NH;

Q=a bond or CH=CH;

n=0, 1, 2, 3 or 4;

M=O, NOH or $H_2$;

Z=H or halogen;

and the pharmaceutically acceptable salts thereof.

The terms "$C_1$–$C_6$ alkyl" and "$C_3$–$C_7$ alkyl" includes straight chain and branched chain hydrocarbons where the alkyl group contains 3 or more carbons. The term "aryl" refers to aromatic moieties having from 6 to 10 carbon atoms. The term "substituted aryl" refers to an aryl group as previously defined having 1 to 3 substituents selected from halogen $CF_3$, nitro, amino, $C_1$–$C_6$ alkyl, —O-($C_1$–$C_6$ alkyl), $C_2$–$C_6$ alkenyl, or CN. The term "aralkyl" refers to an aryl group of 6 to 10 carbons attached to an alkylene group of from 1 to 6 carbons, i.e., $C_6$–$C_{10}$ aryl—$C_1$–$C_6$ alkylene—. The term "substituted aralkyl" refers to an aralkyl group as previously defined where the aryl moiety may be substituted as previously defined under the term "substituted aryl." The term halogen refers to fluorine, chlorine, bromine or iodine. The term $C_4$–$C_8$ cycloalkylidene refers to a $C_4$–$C_8$ cycloalkyl group having an exocyclic double bond.

The term "pharmaceutically acceptable salts" means acid addition salts where they can be formed and basic salts where they can be formed. Acid addition salts can be formed where the invention compound has a basic nitrogen from pharmaceutically acceptable inorganic and organic acids including but not limited to hydrochloric, sulfonic, phosphoric, acetic, maleic, fumaric, succinic, citric, tartaric, and methanesulfonic acids. Basic salts can be formed where the invention compound contains a carboxylic acid group from the alkali metal and alkaline earth hydroxides and ammonia and alkylamines. It will be recognized by those skilled in the art that solid compounds or salts thereof may be isolated as solids containing residual amounts of solvent or water of hydration and are considered to be equivalent to the non-solvated or non-hydrated form.

The preferred examples of the invention may be described by the general formula:

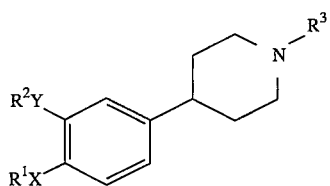

where:

$R^1$=H, $C_1$–$C_3$ alkyl;
$R^2$=$C_4$–$C_6$ alkyl, $C_5$–$C_6$ cycloalkyl or $C_4$–$C_8$ cycloalkylidene when Y is CH:

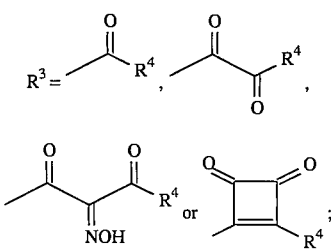

$R^4$=$OR^5$, $NHR^5$, or NHOH;
$R^5$=H, $C_1$–$C_6$ alkyl, aralkyl or

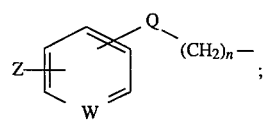

W=N or CH;
X=$CH_2$ or O;
Y=$CH_2$, CH, O, S, or NH;
Q=a bond or CH=CH;
n=0, 1, 2; and
Z=H or halogen.

The most preferred embodiments of the invention are as follows:

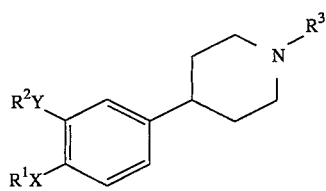

where:
$R^1$=$CH_3$;
$R^2$=$nC_4H_9$,

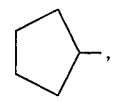

or when Y is CH, $R^2$ is

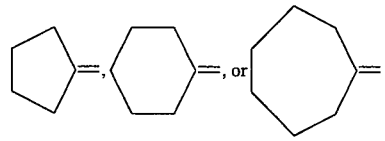

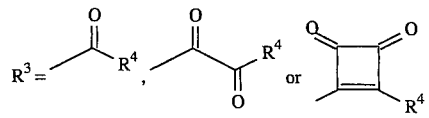

$R^4$=$OR^5$, $NHR^5$ or NHOH;
$R^5$=H, $C_1$–$C_3$ alkyl or

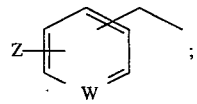

W=N or CH;
X=$CH_2$ or O;
Y=$CH_2$, CH, or O and
Z=H or halogen.

These compounds are inhibitors of the enzyme 3',5'-cyclic AMP phosphodiesterase. It is by virtue of this activity that the compounds act as bronchodilators as well as prevent the influx of leukocytes into the lungs and pulmonary cavities of antigen-sensitized and subsequently challenged laboratory animals. Thus, these compounds are useful for the acute and chronic treatment of bronchial asthma and its associated pathology.

The invention also provides a process for the preparation of a compound having the Formula I

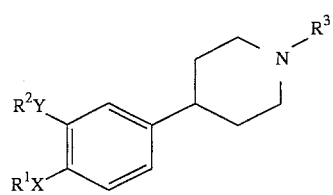

in which $R^1$, $R^2$, $R^3$, X and Y are as defined above or a pharmaceutically acceptable salt thereof, in which a compound having the formula II

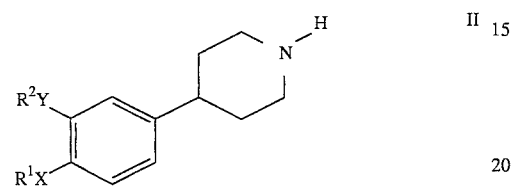

or a salt thereof wherein $R^1$, $R^2$, X and Y are as defined above is reacted with a compound that introduces $R^3$ or a precursor therefor at the piperidine nitrogen atom and, where appropriate, the said precursor is converted into $R^3$ and, if desired, a compound having formula I is converted into a salt thereof.

Compounds having formula II are known per se or can be made by methods known per se. The process of introducing $R^3$ or a precursos therefor at the piperidine nitrogen atom and, where appropriate, the conversion of the precursor into $R^3$ can be carried out by known methods such as, for instance, those illustrated below.

DETAILED DESCRIPTION OF THE INVENTION

The compounds of the invention are prepared from an intermediate 4-(substitutedphenyl)piperidine which may be prepared according to the following reaction sequence.

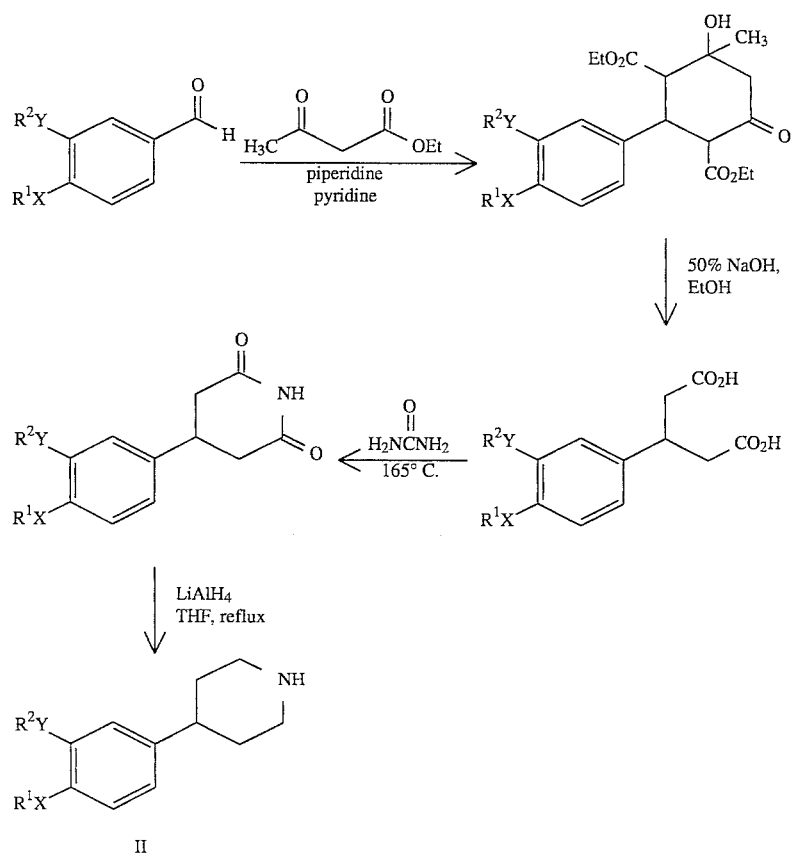

The compounds were $R^3$ is are prepared from the above intermediate according to the following reaction schemes I–V.
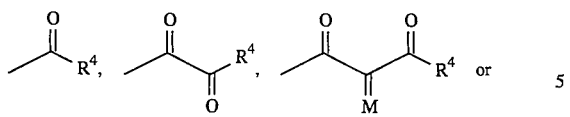
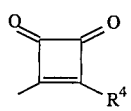
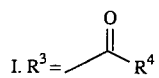
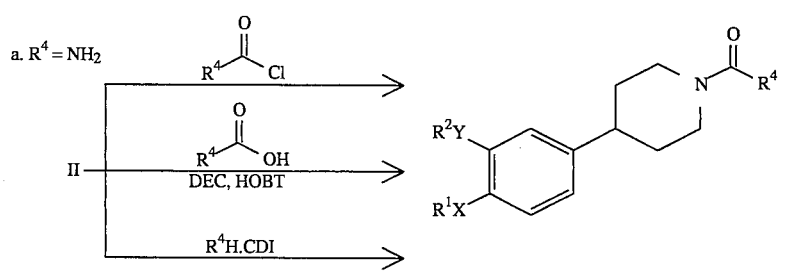
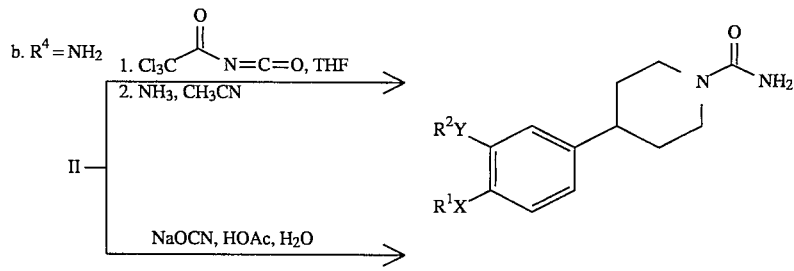
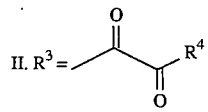
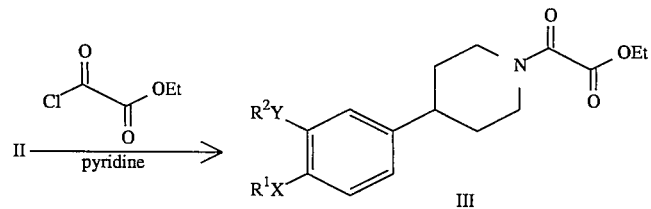
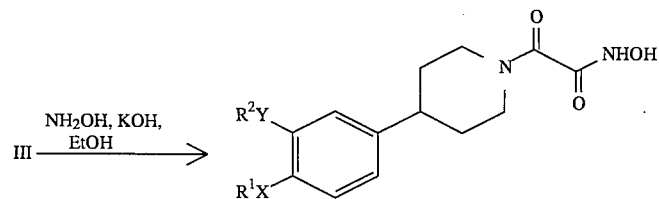

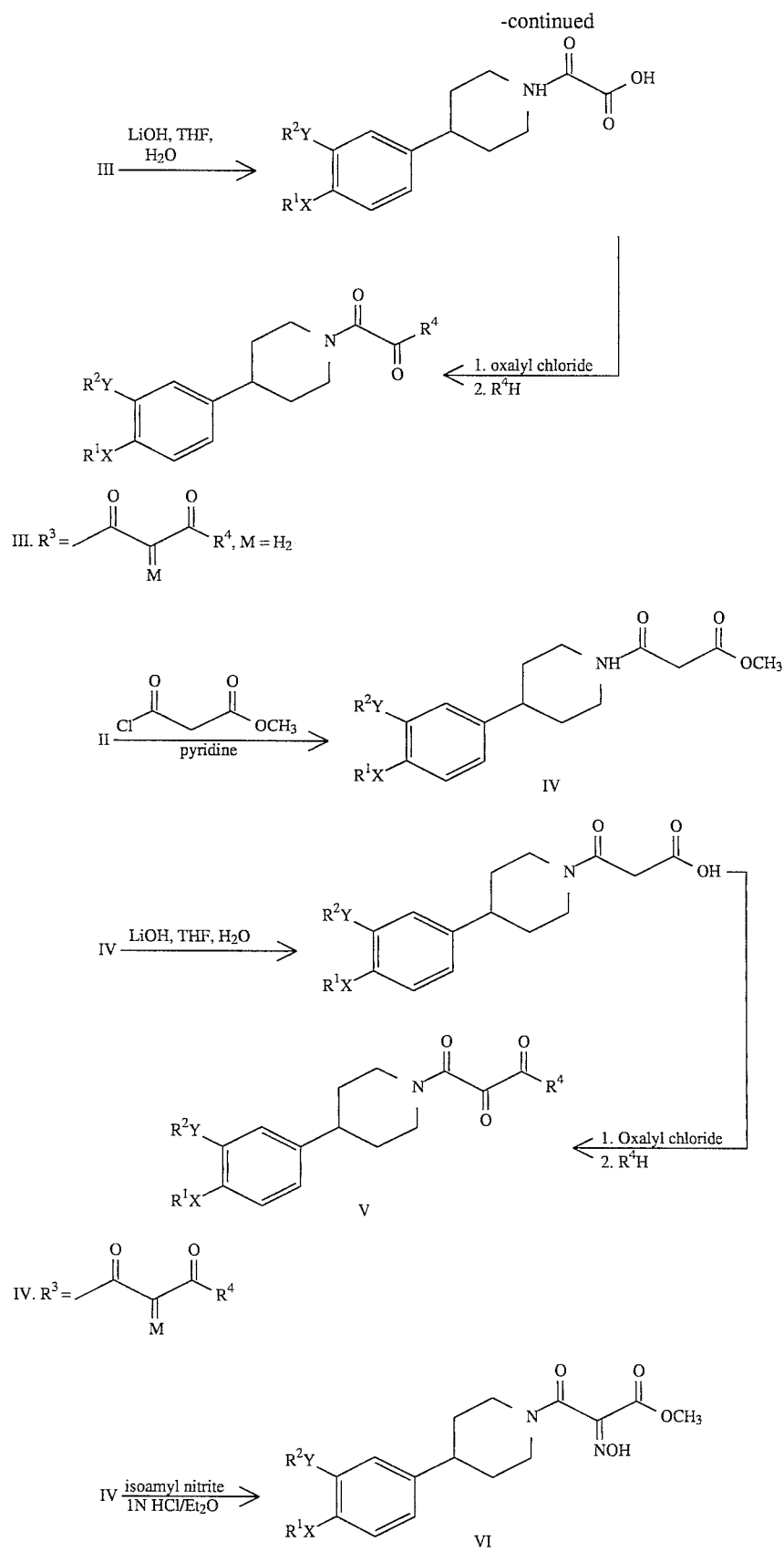

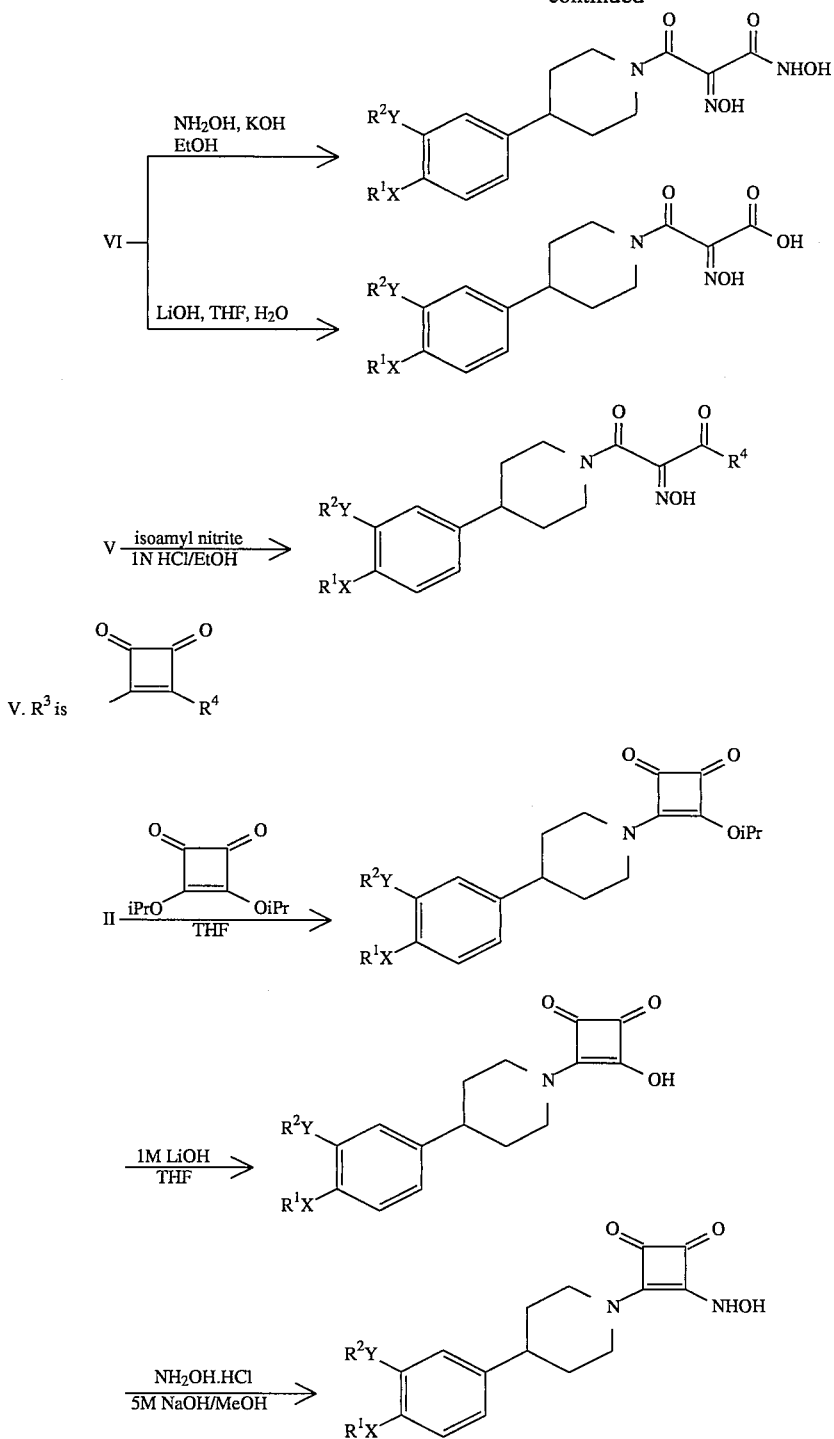
Where Y is CH₂, the starting benzaldehyde may be prepared according to the following reaction scheme, wherein R² is $C_4$–$C_8$ cycloalkyl.

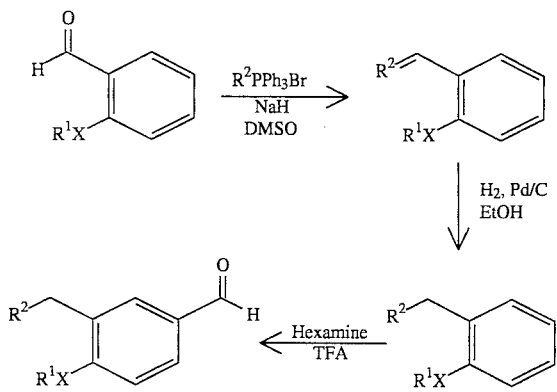

Where Y is O, the starting benzaldehyde may be prepared by alkylation of an appropriate phenol precursor according to the following reaction scheme.

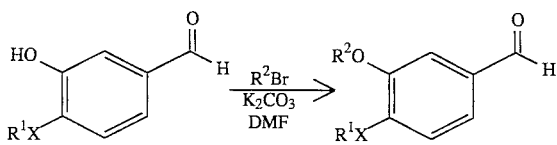

Where Y is CH and $R^2$ is $C_4$–$C_8$ cycloalkylidene, the starting aldehydes may be prepared as follows where p is 0, 1, 2, 3 or 4.

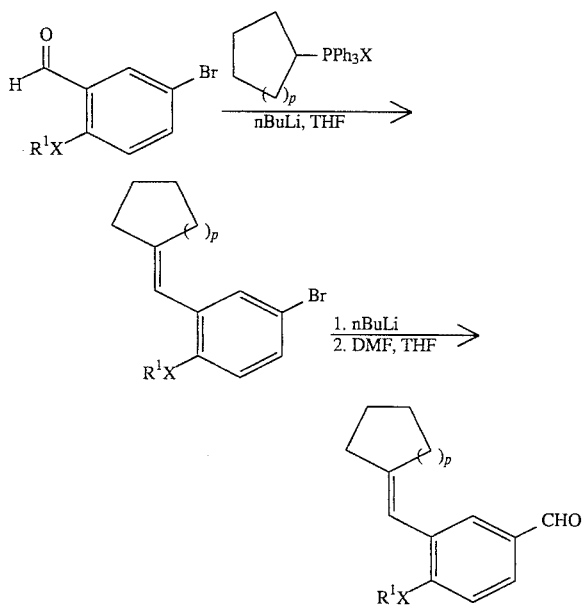

In the synthetic procedures which follow, all materials are either commercially available or can be prepared by literature procedures. Of course, other methods of preparation which are known to those skilled in the art may also be employed to prepare the intermediates and compounds of this invention.

The following procedures illustrate the preparation of the intermediate 4-phenylpiperidines using procedures outlined above.

3-cyclopentyloxy-4-methoxybenzaldeyde

To a magnetically-stirred solution of isovanillin (557 mmol, 85.0 g) in dry DMF (500 mL) at room temperature was added powdered $K_2CO_3$ (558 mmol, 77.1 g) in one portion followed by the dropwise addition of neat cyclopentyl bromide (614 mmol, 91.5 g; 65.9 mL). The resulting suspension was warmed to 60° C. and the reaction monitored by TLC until complete. Upon completion, the reaction mixture was cooled to room temperature and the DMF was removed in vacuo. The residue was partitioned between $H_2O$ and EtOAc, the aqueous phase extracted with EtOAc and the combined organic layers were washed with $H_2O$. The organics were dried ($Na_2SO_4$) and concentrated in vacuo to afford the alkylated product (317 mmol, 70.1 g; 57%) as a viscous oil which was of sufficient purity to be used as such in subsequent transformation.

$^1$H NMR (DMSO-$d_6$, 300 MHz); δ 9.83 (s, 1H), 7.52 (dd, J=8.5; 2.0 Hz, 1H), 7.36 (d, J=2.0 Hz, 1H), 7.16 (d, J=8.5 Hz, 1H), 4.84 (m 1H), 3.83 (s, 3H), 1.70 (m, 8H).

α-3-(3-cyclopentyloxy-4-methoxyphenyl)-β,β-2,4-dicarboethoxy-β-5-hydroxy-α-5-methylcyclohexanone Following the procedure of De and Ghose, *J. Indian Chem. Soc.*, 1976, 53, 1122, reaction of 3-cyclopentyloxy-4-methoxybenzaldehyde (40 mmol, 8.80 g), ethyl acetoacetate (80 mmol, 10.4 g), piperidine (1 mL) and 95% EtOH (2 mL) afforded the title compound as a white solid, mp=145°–147° C. (15.2 g, 82%).

$^1$H NMR (DMSO-$d_6$, 400 MHz) δ 6.88 (d, 1H, J=2 Hz); 6.81 (d, 1H, J=8 Hz); 6.76 (dd, 1H, J=8 Hz, 2 Hz); 4.83 (s, 1H); 4.71 (m, 1H); 3.85 (m, 6H); 3.68 (s, 3H); 3.26 (d, 1H, J=12 Hz); 2.90 (d, 1H, J=14 Hz); 2.31 (d, 1H, J=14 Hz); 1.84 (m, 2H); 1.68 (m, 4H); 1.55 (m, 2H); 1.23 (s, 3H); 0.97 (t, 3H, J=7 Hz); 0.87 (t, 3H, J=7 Hz).

3-(3-cyclopentyloxy-4-methoxyphenyl)glutaric Acid

Following the procedure of De and Ghose, *Vide Supra,* reaction of α-3-(3-cyclopentyloxy-4-methoxyphenyl)-β,β -2,4-dicarboethoxy-β-5-hydroxy-α-5-methylcyclohexanone (21.6 mmol, 10.0 g) in NaOH (50% by weight, 100 mL) and 90% EtOH (100 mL) afforded the diacid as a white solid, mp=173°–174° C. (5.91 g, 85%).

$^1$H NMR (DMSO-$d_6$, 400 MHz) δ 12.02 (s, 2H); 6.82 (m, 2H); 6.73 (dd, 1H, J=8 Hz, 2 Hz); 4.75 (m, 1H); 3.69 (s, 3H); 3.35 (m, 1H); 2.60 (dd, 2H, J=16 Hz, 6 Hz); 2.45 (m, 2H); 1.85 (m, 2H); 1.68 (m, 4H); 1.57 (m, 2H).

4-(3-cyclopentyloxy-4-methoxyphenyl)-2,6-piperidinedione

Following the procedure of Nacci et al, *Farmaco. Ed. Sci.* 1973, 328, 399, fusion of 3-(3-cyclopentyloxy-4 -methoxyphenyl)glutaric acid (23.1 mmol, 7.5 g) and urea (69.5 mmol, 4.17 g) at 165° C. for 1 hour gave, after trituration with $CH_2Cl_2$, the title compound as a tan solid (4.18 g, 60%) of sufficient purity for subsequent transformations.

An analytical sample could be prepared by filtering the crude material through a plug of $SiO_2$ (10% EtOAc/$CH_2Cl_2$ eluent) to afford the title compound as a white solid mp=152°–153° C.

$^1$H NMR (DMSO-d6, 400 MHz) δ 10.79 (s, 1H); 6.87 (m, 2H); 6.76 (dd, 1H, J=8 Hz, 2 Hz); 4.76 (m, 1H); 3.70 (s, 3H); 3.33 (m, 1H); 2.77 (dd, 2H, J=17 Hz, 11 Hz); 2.61 (dd, 2H,

J=17 Hz, 4 Hz); 1.87 (m, 2H); 1.68 (m, 4H); 1.55 (m, 2H).

4-(3-cyclopentyloxy-4-methoxyphenyl)piperidine

Following the procedure of Nacci et al, *Vide Supra,* reaction of 4(3-cyclopentyloxy-4-methoxyphenyl)-2,6 -piperidinedione (12 mmol, 3.65 g) and lithium aluminum hydride (120 mmol, 4.56 g) in dry THF (240 mL) afforded the title compound as a light yellow waxy solid (2.71 g, 82%) of sufficient purity for subsequent transformations.

An analytical sample could be prepared by reaction of equimolar portions of the crude amine and maleic acid in acetone and crystallization of the resulting salt from $Et_2O$ and acetone. The maleate salt is a white solid with a mp of 142°–143° C.

Spectral Data of Maleate Salt $^1$H NMR (DMSO-$d_6$, 400 MHz) δ 8.35 (m, 2H); 6.88 (d, 1H, J=8 Hz); 6.74 (d, 1H, J=2 Hz); 6.71 (dd, 1H, J=8 Hz, 2 Hz); 6.02 (s, 2H); 4.76 (m, 1H); 3.70 (s, 3H); 3.37 (m, 2H); 2.97 (td, 2H, J=3 Hz, 13 Hz); 2.74 (m, 1H); 1.95–1.5 (m, 12H).

IR (KBR, cm$^{-1}$) 3420, 2960, 1565, 1515, 1375, 1250, 1235, 1150, 1135, 1030, 990, 865.

MS (EI, m/e (%)) 276 (100, M+); 208 (77); 192 (15); 164 (10).

Analysis Calc'd for $C_{21}H_{29}NO_6$: C, 64.43; H, 7.46; N, 3.57. Found: C, 64.36; H, 7.34; N, 3.24.

1-cyclopentylidenemethyl-2-methoxybenzene

A suspension of sodium hydride (608 mmol, 24.3 g; 60% dispersion in oil) in dry DMSO (3L) was heated to 60° C. for one hour and cooled to an internal temperature of 42° C. Cyclopentyltriphenylphosphonium bromide (608 mmol, 250 g) was added in one portion and to the resulting red solution was added 2-methoxybenzaldehyde (669 mmol, 91.0 g; 80.7 mL) dropwise over a few minutes. The dark reaction mixture was heated to 60° C. for 18 hours and cooled to room temperature. The reaction was diluted with water (4L), extracted with $CH_2Cl_2$ (2×3L) and concentrated in vacuo. The residue was partitioned between 15:1 hexane/EtOAc (1.3L) and water (1.6L), the organics washed with water (3×600 mL), dried ($Na_2SO_4$) and concentrated in vacuo. Upon concentration, triphenylphosphine oxide crystallized out of solution. The suspension was diluted with hexane, the solids removed by filtration, and the filtrate concentrated in vacuo to afford a dark oil. This material was vacuum distilled to afford the title compound as a light yellow oil (76.7 g, 67%). The desired material comes over at 90°–97° C. at 0.05 mm Hg and is used as such in the subsequent transformation.

1-cyclopentylmethyl-2-methoxybenzene

A mixture of 1-cyclopentylidenemethyl-2-methoxybenzene (408 mmol, 76.7 g) and 10% Pd on carbon (7.67 g, 10% by weight) in absolute EtOH (767 mL) was shaken at room temperature under 54 psig of hydrogen pressure for 2.5 hours. Additional $H_2$ was added to the vessel as necessary to maintain the initial pressure. The volatiles were removed in vacuo and the residue vacuum distilled to afford the title compound as a colorless oil (72.7 g, 94%). The desired fraction comes over at 85°–95° at 2.0–2.5 mm Hg and is used as such in the subsequent transformation.

3-cyclopentylmethyl-4-methoxybenzaldeyde

To a stirred mixture of 1-cyclopentylmethyl-2-methoxybenzene (383 mmol, 72.7 g) in trifluoroacetic acid (3.83 mol, 435 g; 294 mL) was added hexamine (766 mmol, 107 g) in one portion at room temperature, resulting in an exothermic reaction. After the exotherm had subsided, the reaction mixture was heated to 100° C. for 18 hours and cooled to room temperature. The heterogenous mixture was diluted with $CH_2Cl_2$ (800 mL) and the resulting homogenous solution was cooled to 0° C. and neutralized to pH 7 by the dropwise addition of 2.5N NaOH (~1L). The layers were separated, the aqueous phase extracted with $CH_2Cl_2$ (1×600 mL), dried ($Na_2SO_4$), and concentrated in vacuo to afford a viscous oil. Purification by filtration through a plug of $SiO_2$ (gradient elution: 1) hexane, 2) 36:1 hexane/EtOAc, 3) 18:1 hexane/EtOAc, 4) 12:1 hexane/EtOAc, 5) 8:1 hexane/EtOAc) afforded the title compound as a light yellow oil (46.6 g, 56%).

$^1$H NMR (DMSO-$d_6$, 300 MHz); δ 9.82 (s, 1H); 7.75 (dd, 1H, J=8.5; 2.0 Hz); 7.65 (d, 1H, J=2.0 Hz); 7.15 (d, 1H, J=8.5 Hz); 3.85 (s, 3H); 2.60 (d, 2H, J=7 Hz); 2.10 (m, 1H); 1.55 (m, 6H); 1.15 (m, 2H).

α-3-(3-cyclopentylmethyl-4-methoxyphenyl)-β,β-2,4-dicarboethoxy-β-5-hydroxy-α-5-methylcyclohexanone Following the procedure of De and Ghose, J. Indian Chem. Soc., 1976, 53, 1122, reaction of 3-cyclopentylmethyl-4-methoxybenzaldehyde (45.8 mmol, 10.0 g), ethyl acetoacetate (92.0 mmol, 12.0 g), piperidine (1.1 mL) and 95% EtOH (3 mL) afforded the title compound as a white solid (13.9 g, 66%).

$^1$H NMR (DMSO-$d_6$, 300 MHz) δ 7.05 (m, 2H); 6.80 (m, 1H); 4.85 (m, 1H); 3.80 (m, 9H); 3.28 (m, 4H); 2.93 (d, 1H); 2.48 (m, 2H); 2.31 (d, 1H), 2.05 (m, 1H), 1.55 (m, 5H); 1.25–0.80 (m, 9H).

3-(3-cyclopentylmethyl-4-methoxyphenyl)glutaric Acid

Following the procedure of De and Chose, *Vide Supra,* reaction of α-3-(3-cyclopentylmethyl-4 -methoxyphenyl)-β,β-2,4-dicarboethoxy-β-5-hydroxy-α-5-methylcyclohexanone (30.2 mmol, 13.9 g) in NaOH (50% by weight, 151 mL) and 90% EtOH (151 mL) afforded the diacid as a white solid, mp=123°–125° C. (9.2 g, 95%).

$^1$H NMR (DMSO-$d_6$, 300 MHz) δ 12.02 (s, 2H); 7.00 (m, 2H); 6.80 (m, 1H); 3.72 (s, 3H); 3.33 (m, 1H); 2.64–2.40 (m, 6H); 2.05 (m, 1H); 1.64–1.10 (m, 8H).

4-(3-cyclopentylmethyl-4-methoxyphenyl)-2,6-piperidinedione

Following the procedure of Nacci et al., *Farmaco Ed. Sci.* 1973, 328, 399, fusion of 3-(3-cyclopentylmethyl-4 -methoxyphenyl)glutaric acid (28.6 mmol, 9.16 g) and urea (85.8 mmol, 5.15 g) at 165° C. for 1 hour gave, after trituration with $CH_2Cl_2$ followed by filtration through a plug of $SiO_2$ (40% EtOAc/hexane eluent), the title compound as a white solid, mp=133.5°–134.5° C. (6.33 g, 73%), of sufficient purity for subsequent transformations.

$^1$H NMR (DMSO-$d_6$, 300 MHz) δ 10.80 (s, 1H); 7.06 (m, 2H); 6.88 (m, 1H); 3.74; (s, 3H) 3.30 (m, 1H); 2.80–2.48 (m, 6H); 2.06 (m, 1H); 1.64–1.40 (m, 6H); 1.15 (m, 2H).

4-(3-cyclopentylmethyl-4-methoxyphenyl)piperidine

Following the procedure of Nacci et al, *Vide Supra*, reaction of 4-(3-cyclopentylmethyl-4-methoxyphenyl)-2,6-piperidinedione (20.0 mmol, 6.0 g) and lithium aluminum hydride (209 mmol, 7.94 g) in dry THF (130 mL) afforded the title compound as a white, waxy solid (4.85 g, 89%) of sufficient purity for subsequent transformations.

An analytical sample could be prepared by reaction of equimolar portions of the crude amine and maleic acid in acetone and crystallization of the resulting salt from Et$_2$O and acetone. The maleate salt is a white solid with a mp of 168°–169° C.

Spectral Data of Maleate Salt $^1$H NMR (DMSO-d$_6$, 400 MHz) δ 8.35 (m, 2H); 6.99 (dd, 1H, J=8 Hz, 2 Hz); 6.94 (d, 1H, J=2 Hz); 6.87 (d, 1H, J=8 Hz); 6.01 (s, 2H); 3.73 (s, 3H); 3.37 (m, 2H); 2.97 (td; 2H, J=13 Hz, 3 Hz); 2.74 (m, 1H); 2.53 (m, 2H); 2.06 (m, 1H); 1.88 (m, 2H); 1.72 (m, 2H); 1.58 (m, 4H); 1.46 (m, 2H); 1.16 (m, 2H).

IR (KBr, cm$^{-1}$) 3410 (br), 3000, 2940, 2860, 2820, 1640, 1560, 1495, 1460, 1445, 1370, 1240, 1110, 1030, 860, 810, 755.

MS ((+)-PBCI, m/e (%)) 274 (100, [M+H[$^+$, free base).

Anal. calc'd for C$_{22}$H$_{31}$NO$_5$: C, 67.84; H, 8.02; N, 3.60. Found: C, 67.96; H, 7.96; N, 3.59.

4-bromo-2-cyclopentylidenemethylanisole

A one liter single-necked round bottom flask was flame dried, cooled and charged with cyclopentyltriphenylphosphonium bromide (55 g, 133 mmol). The bromide was evacuated under high vacuum (approx. 0.2 mmHg) for 15 minutes. THF (400 ml, dry) was added and the resulting suspension was cooled and stirred under nitrogen at 0° C. n-Butyllithium (51.16 ml, 127.9 mmol) was added rapidly resulting in a reddish brown solution*.

*Initial addition of base (5 ml) showed no ylide formation (color change) so a volume of base equal to the volume added which caused sustained reaction color change was added at the end (in this case 5 ml). The reaction was stirred for 15 minutes at 0° C. A pressure equalizing funnel was charged with a solution of 5-bromo-o-anisaldehyde (25 g, 116.3 mmol) in THF (125 ml). The aldehyde was added rapidly with reaction temperature rising as high as 50° C. The addition funnel was rinsed with THF (50 ml). The reaction was titrated to completion with small amounts of solid aldehyde (600 mg, 2.79 mmol). Saturated NH$_4$Cl was added to quench the reaction. The reaction mixture was concentrated to dryness. The produce was triturated with ethyl acetate/hexane (1:4, 3×500 ml), concentrated to dryness, then distilled (bp=140°–144° C., 0.15 mmHg) to give the title compound in 89% yield as a clear oil (28.4 g, 106.3 mmol).

NMR(DMSO): δ7.37 (d, 1H), J=2.7 Hz) 7.32 (dd, 1H, J=8.72 Hz, 2.49 Hz), 6.92 (d, 1H, J=8.93 Hz), 6.41 (m, 1H), 3.76 (s, 3H), 2.42 (m, 4H), 1.66 (m, 4H).

IR(Film, cm$^{-1}$) 2960(s), 1480(s), 1245(s).

MS(DCI): m/z=267 (M+H)$^+$, m/z=267, 269 (1 Br present).

Anal. Calcd for C$_{13}$H$_{15}$OBr: C, 58.44; H, 5.66 Found: C, 58.31; H, 5.58.

3-cyclopentylidenemethyl-4-methoxybenzaldehyde 4-bromo-2-cyclopentylidenemethylanisole (738 mg, 2.5 mmol) in THF (20 ml) was cooled to −78° C. while stirring under nitrogen. n-Butyllithium (1 ml, 2.5M in Hexane, 2.5 mmol) was added dropwise over 1 minute. N,N-Dimethylformamide (0.5 ml) was added rapidly. The ice bath was removed an the reaction was warmed to room temperature. The reaction was diluted with ethyl acetate (100 ml) and was washed with water (50 ml) and brine (50 ml). The organic was dried over MgSO$_4$, filtered and concentrated. The product was purified via flash chromatography. The yield of the title compound (440 mg, 1.8 mmol) was 72%.

NMR (DMSO): δ9.87 (s, 1H), 7.82 (dd, 1H, J=8.5 Hz, 2.07 Hz), 7.16 (d, 1H, J= 8.5 Hz), 6.49 (m, 1H), 3.88 (s, 3H), 2.45 (m, 4H), 1.63 (m, 4H).

IR (KBR, cm$^{-1}$): 2970(s), 1695(s), 1600(s), 1260(s).

MS (PBEI): m/z=216(M)$^-$

Anal. Calcd for C$_{14}$H$_{16}$O$_2$: C, 77.75; H, 7.46 Found: C, 77.7; H, 7.67.

α-3-(3-cyclopentylidenemethyl-4-methoxyphenyl)-β,β-2,4-dicarboethoxy-β-5-hydroxy-α-5-methylcyclohexanone Reaction of 3-cyclopentylidenemethyl-4-methoxy-benzaldehyde (22.7 mmol, 4.9 g), ethylacetoacetate (45.3 mmol, 5.9 g), piperidine (560 µL) and 95% ethanol (1.5 mL) afforded a white solid (14.7 mmol, 6.74 g, 65%).

$^1$H NMR (DMSO-d$_6$, 300 MHz) δ 7.24 (d, 1H); 7.05 (dd, J=8.5; 2.0 Hz, 1H); 6.82 (d, 1H); 6.41 (m, 1H); 3.82 (m, 6H); 3.71 (s, 3H); 3.26 (d, 1H); 2.94 (d, 1H); 2.42 (m, 4H); 2.31 (d, 1H); 1.65 (m, 4H); 1.23 (s, 4H); 0.97 (t, 3H); 0.87 (t, 3H).

4-(3-Cyclopentylidenemethyl-4-methoxy-phenyl)glutaric Acid

Following the procedure of De and Ghose, *Vide Supra*, reaction of the ester (17.4 mmol, 8.0 g) in NaOH (50% by weight, 87 mL) and EtOH (90%, 87 mL) afforded the diacid as a yellow solid (16.4 mmol, 5.21 g, 94%).

$^1$H NMR (DMSO-d$_6$, 300 MHz) δ 11.90 (br s, 2H); 7.03 (d, 1H); 6.91 (dd, J=8.5; 2.0 Hz, 1H); 6.70 (d, 1H); 6.31 (m, 1H); 3.60 (s, 3H); 3.22 (m, 1H); 2.47 (d, 4H); 2.32 (m, 6H); 1.51 (m, 4H).

4-(3-cyclopentylidenemethyl-4-methoxyphenyl)-2,6-piperidindione

Following the procedure of De and Ghose, *Vide Supra*, fusion of the diacid (16.4 mmol, 5.2 g) and urea (49.2 mmol, 2.95 g) at 165° C. for 1 hour gave, after trituration with CH$_2$Cl$_2$, a tan solid (12.3 mmol, 3.68 g, 75%).

An analytical sample could be prepared by filtering the crude material through a plug of SiO$_2$ (40% EtOAc/hexane) to afford the title compound as a white solid (9.7 mmol, 2.9 g, 59%).

$^1$H NMR (DMSO-d$_6$, 300 MHz) δ 10.80 (s, 1H); 7.21 (d, 1H); 7.08 (dd, J=8.5; 2.0 Hz, 1H); 6.90 (d, 1H); 6.46 (m, 1H); 3.73 (s, 3H); 3.38 (m, 1H); 2.7 (m, 4H); 2.41 (m, 4H); 1.64 (m, 4H).

4-(3-Cyclopentylidenemethyl-4-methoxy-phenyl)-piperidine

Following the procedure of Nacci et al, *Farmaco. Ed. Sci.* 328, 1973, 399, reaction of the imide (9.7 mmol, 2.9 g) and lithium aluminum hydride (97 mmol, 3.7 g) in dry THF (70 mL) afforded the title compound as an oil (8.5 mmol, 2.3 g, 87%) of sufficient purity for subsequent transformations.

An analytical sample could be prepared by reaction of equimolar portions of the crude amine and maleic acid in acetone and crystallization of the resulting salt from acetone and Et$_2$O. The maleate salt is a white solid.

$^1$H NMR (DMSO-d$_6$, 400 MHz) δ 8.43 (br s, 2H); 7.15 (d, 1H); 7.01 (dd, J=8.5; 2.0 Hz, 1H); 6.90 (d, 1H); 6.48 (m, 1H); 6.02 (s, 2H); 3.74 (s, 3H); 3.38 (m, 2H); 2.97 (m, 2H);

2.76 (m, 1H); 2.43 (m, 4H); 1.90 (m, 2H); 1.68 (m, 6H).

IR (KBr (cm⁻¹)) 3420 (br), 2950, 1560, 1485, 1365, 1235, 1110, 1025, 860, 810.

MS (EI, m/e (%)) 271 (20, M⁺), 240(5), 229(5), 215(5), 171(5), 147(10), 115(12), 91(10), 84(15), 83(40), 82(15), 68(10), 58(20), 57(100), 56(68), 43(39).

Anal. Calc'd for: $C_{22}H_{29}NO_5$: C, 68.20; H, 7.54; N, 3.61. Found: C, 67.63; H, 7.58; N, 3.58.

4-bromo-2-cycloheptylidenemethylanisole

This material was prepared following the procedure for 4-bromo-2-cyclopentylidenemethylanisole, Vide Supra, to afford the title compound in 97% yield.

NMR (DMSO): δ7.35 (dd, 1H, J=8.71 Hz, 2,28 Hz), 7.23 (t, 1H, J=0.42 Hz, 2.08 Hz), 6.92 (d, 1H, J=8.72 Hz), 6.18 (s, 1H), 3.75 (s, 3H), 2.33 (m, 4H), 1.59 (m, 4H), 1.50 (m, 4H).

IR (Film, cm⁻¹): 2910(s), 2840(m), 1475(s), 1240(s).

MS (PBEI): m/z=294(M)⁻, m/z=294, 296 (1 Br present).

Anal. Calcd for $C_{15}H_{19}OBr$: C, 61.03, H, 6.49. Found: C, 61.60; H, 6.42.

3-cycloheptylidenemethyl-4-methoxybenzaldehyde 4-bromo-2-cycloheptylidenemethylanisole (738 mg, 2.5 mmol) in THF (20 ml) was cooled to −78° C. while stirring under nitrogen. n-Butyllithium (1 ml, 2.5M in Hexane, 2.5 mmol) was added dropwise over 1 minute. N,N-Dimethylformamide (0.5 ml) was added rapidly. The ice bath was removed an the reaction was warmed to room temperature. The reaction was diluted with ethyl acetate (100 ml) and was washed with water (50 ml) and brine (50 ml). The organic solution was dried over $MgSO_4$, filtered and concentrated. The product was purified via flash chromatography to yield 440 mg (1.8 mmol) of the title compound (72%).

NMR (DMSO): δ9.86 (s, 1H), 7.80 (dd, 1H, J=8.51 Hz, 2.07 Hz), 7.67 (d, 1H, J= 2.28 Hz), 7.18 (d, 1H, J=8.51 Hz), 6.25 (s, 1H), 3.87 (s, 3H), 2.35 (m, 4H), 1.61 (m, 4H), 1.52 (m, 4H).

IR (KBr, cm⁻¹): 2910(s), 2840(s), 1680(s), 1585(s), 1250(s).

MS (PBEI): m/z=244(M)⁺

Anal. Calcd for $C_{16}H_{20}O_2$: C, 78.65; H, 8.25. Found: C, 76.89; H, 7.33.

α-3-(3-cycloheptylidenemethyl-4-methoxyphenyl)-β,β-2,4-dicarboethoxy-β-5-hydroxy-α-5-methylcyclohexanone Reaction of the aldehyde (24.1 mmol, 5.9 g), ethylacetoacetate (48.2 mmol, 6.1 mL), piperidine (595 μL) and 95% ethanol (1.6 mL) afforded a white solid (14.0 mmol, 6.83 g, 58%).

¹H NMR (DMSO-$d_6$, 300 MHz) δ 7.15 (dd, J=8.5; 2.0 Hz, 1H); 7.06 (d, 1H); 6.84 (d, 1H); 6.19 (s, 1H); 3.82 (m, 6H); 3.70 (s, 3H); 3.24 (d, 1H); 2.93 (d, 1H); 2.32 (m, 6H); 1.55 (m, 7H); 1.22 (s, 4H); 0.96 (t, 3H); 0.87 (t, 3H).

4-(3-Cycloheptylidenemethyl-4-methoxy-phenyl)-glutaric Acid

Following the procedure of De and Ghose, Vide Supra, reaction of the ester (14.0 mmol, 6.83 g) in NaOH (50% by weight, 70 mL) and ethanol (90%, 70 mL) afforded the diacid as a yellow solid (11.9 mmol, 4.12 g, 85%).

¹H NMR (DMSO-$d_6$, 300 MHz) δ 12.01 (s, 2H); 7.05 (m, 2H); 6.83 (d, 1H); 6.21 (s, 1H); 3.70 (s, 3H); 3.36 (m, 1H); 2.61 (dd, J=16.8; 6.0 Hz, 2H); 2.44 (dd, J=15.6; 8.4 Hz, 2 H); 2.33 (m, 4H); 1.56 (m, 8H).

4-(3-Cycloheptylidenemethyl-4-methoxy-phenyl)-2,6-piperidinedione

Following the procedure of De and Ghose, Vide Supra, fusion of the diacid (11.9 mmol, 4.1 g) and urea (35.7 mmol, 2.14 g) at 165° C. for 1.5 hours gave, after trituration with $CH_2Cl_2$, a tan solid which was further purified through a plug of $SiO_2$ (175 g, 40% EtOAc/hex) to afford the title compound (9.5 mmol, 3.1 g, 80%).

¹H NMR (DMSO-$d_6$, 300 MHz) δ 10.80 (s, 1H); 7.10 (m, 2H); 6.91 (d, 1H); 6.21 (s, 1H); 3.72 (s, 3H); 3.37 (m, 1H); 2.76 (dd, J=18.0; 10.8 Hz, 2H); 2.63 (dd, J=16.8; 4.8 Hz, 2 H); 2.35 (m, 4H); 1.55 (m, 8H).

4-(3-Cycloheptylidenemethyl-4-methoxy-phenyl)-piperidine Maleate Salt (1:1)

Following the procedure of Nacci et al, Farmaco. Ed. Sci. 328, 1973, 399, reaction of the imide (9.5 mmol, 3.1 g) and lithium aluminum hydride (95.0 mmol, 3.61 g) in dry THF (70 mL) afforded the title compound as a clear oil (6.8 mmol, 2.04 g, 72%).

An analytical sample could be prepared by reaction of equimolar portions of the crude amine and maleic acid in acetone and trituration of the resulting salt in acetone/$Et_2O$ to yield the maleate salt as a white solid.

¹H NMR (DMSO-$d_6$, 400 MHz) δ 7.10 (dd, J=24.0; 6.0 Hz, 1H); 6.96 (d. 1H); 6.84 (d, 1H); 6.24 (s, 1H); 3.70 (s, 3H); 2.98 (d, 2H); 2.50 (m, 4H); 2.32 (m, 4H); 1.52 (m 12H).

IR (KBr, (cm⁻¹)) 3420 (br), 2930, 1640, 1565, 1490, 1370, 1240, 1120, 1030, 860, 810.

MS (DEI, m/e (%)) 299 (100, M⁺), 147 (26), 105 (22), 91 (34), 83 ( 70), 57 (82).

Anal. calc'd for $C_{24}H_{33}NO_5$: C, 69.37; H, 8.00; N, 3.37. Found: C, 69.11; H, 7.87; N, 3.32.

The novel compounds of this invention are prepared according to the following illustrative procedures:

EXAMPLE 1

4-(3-cyclopentyloxy-4-methoxyphenyl)piperidine-1-carboxylic Acid Amide

To a stirred solution of 4-(3-cyclopentyloxy-4-methoxyphenyl)piperidine (3.63 mmol, 1.00 g) in dry THF (40 mL) at 0° C. was added trichloroacetylisocyanate (4.72 mmol, 0.889 mg; 563 μL) dropwise over 5 minutes. The resulting solution was stirred at 0° C. for 1 hour and at room temperature for 30 minutes. The reaction was diluted with $NH_3$ saturated $CH_3CN$ solution (40 mL) and stirred at room temperature over the weekend. The volatiles were removed in vacuo and the residue partitioned between EtOAc (100 mL) and water (100 mL). The aqueous phase was extracted with EtOAc (1×100 mL), the combined organics washed with water (1×100 mL), dried ($Na_2SO_4$), and concentrated in vacuo. The crude product was purified by flash chromatography ($SiO_2$:EtOAc) to afford the title compound as a white solid, mp=149°–150° C. (0.800 g, 70%).

¹H NMR (DMSO-$d_6$, 400 MHz) δ 6.83 (d, 1H, J=8 Hz); 6.75 (d, 1H, J=2 Hz); 6.69 (dd, 1H, J=8 Hz, 2 Hz); 5.88, (s, 2H); 4.77 (m, 1H); 4.03 (m, 2H); 3.68 (s, 3H); 2.68 (m, 2H); 2.55 (m, 1H); 1.84 (m, 2H); 1.67 (m, 6H); 1.55 (m, 2H); 1.41 (m, 2H).

IR (KBr, cm$^{-1}$) 3400, 3330, 3190, 2940, 1640, 1590, 1515, 1440, 1260, 1230, 1160, 1135, 1100, 1025, 810.

MS (EI, m/e (%)) 318 (20, M$^+$); 275 (19); 250 (43); 233 (59); 164 (62); 150 (63); 83 (94); 69 (100).

Analysis Calculated for $C_{18}H_{26}N_2O_3$: C, 67.90; H, 8.23; N, 8.80. Found: C, 67.55; H, 8.07; N, 8.70.

EXAMPLE 2

4-(3-cyclopentyloxy-4-methoxyphenyl)piperidine-1-carboxylic Acid Methyl Ester

To a stirred solution of 4-(3-cyclopentyloxy-4-methoxyphenyl)piperidine (1.00 mmol, 0.275 g) and pyridine (1.65 mmol, 0.130 g; 133 µL) in dry CH$_2$Cl$_2$ (10 mL) at 0° C. was added methyl chloroformate (1.10 mmol, 0.104 g; 85 µL) dropwise over 5 minutes. The resulting solution was warmed to room temperature and stirred for 1 hour. The reaction was diluted with CH$_2$Cl$_2$ (70 mL) and extracted with water (70 mL). The aqueous phase was extracted with CH$_2$Cl$_2$ (70 mL), the combined organics washed with water (70 mL), dried (Na$_2$SO$_4$) and concentrated in vacuo. The crude oil was purified by flash chromatography (SiO$_2$: 1) CH$_2$Cl$_2$, 2) 5% EtOAc/CH$_2$Cl$_2$) to afford the title compound as a colorless oil (0.190 g, 57%).

$^1$H NMR (DMSO-d$_6$, 400 MHz) δ 6.83 (d, 1H, J=8 Hz); 6.77 (d, 1H, J=2 Hz); 6.70 (dd, 1H, J=8 Hz, 2 Hz); 4.76 (m, 1H); 4.06 (m, 2H); 3.68 (s, 3H); 3.59 (s, 3H); 2.82 (m, 2H); 2.59 (m, 1H, J=12 Hz, 4H); 190–1.40 (m, 12H).

IR (film, cm$^{-1}$) 2940, 2860, 1700, 1510, 1470, 1440, 1405, 1245, 1210, 1130, 1115, 1015, 985, 760.

MS (EI, m/e (%)) 333 (41, M$^+$): 265 (86); 250 (87); 233 (33); 115 (100).

Analysis Calculated for $C_{19}H_{27}NO_4$: C, 68.44; H, 8.16; N, 4.20. Found: C, 68.22; H, 7.93; N, 4.17.

EXAMPLE 3

4-[3-(cyclopentyloxy)-4-methoxyphenyl]-1-[(E)-1-oxo-3-phenyl-2-propenyl]piperidine A mixture of trans-cinnamic acid (1.20 mmol, 0.178 g), 1-(3-dimethylaminopropyl)-3-ethylcarbodiimide (DEC; 1.20 mmol, 0.230 g) and hydroxybenzotriazole (HOBT; 1.20 mmol, 0.162 g) was dissolved in dry CH$_2$Cl$_2$ (20 mL) and stirred at room temperature for 1.5 hours. To this solution was added 4-(3-cyclopentyloxy-4-methoxyphenyl)piperidine (1.00 mmol, 0.275 g) in dry CH$_2$Cl$_2$ (10 mL) dropwise over 10 minutes and the resulting solution was stirred at room temperature overnight. The volatiles were removed in vacuo and the residue was partitioned between EtOAc (70 mL) and 1N NaOH (70 mL). The aqueous phase was extracted with EtOAc (1×70 mL), the combined organics washed with H$_2$O (1×70 mL), dried (Na$_2$SO$_4$) and concentrated in vacuo to yield a colorless oil. Purification by flash chromatography (SiO$_2$: 5% EtOAc/CH$_2$Cl$_2$) afforded the title compound as a white solid, mp=93°–95° C. (0.385 g, 95%).

$^1$H NMR (DMSO-d$_6$, 400 MHz) δ 7.71 (dd, 2H, J=8 Hz, 2 Hz); 7.48 (d, 1H, J= 15 Hz); 737 (m, 3H); 7.30 (d, 1H, J=15 Hz); 6.84 (d, 1H, J=8 Hz); 6.79 (d, 1H, J=2 Hz); 6.71 (dd, 1H, J=8 Hz, 2 Hz); 4.77 (m, 1H); 4.63 (m, 1H); 4.41 (m, 1H); 3.68 (s, 3H); 3.14 (m, 1H); 2.70 (m, 2H); 1.81 (m, 4H); 1.67 (m, 4H); 1.54 (m, 4H).

IR (KBr, cm$^{-1}$) 3420 (br), 2930, 1650, 1605, 1510, 1430, 1250, 1200, 1135, 1020, 980, 760.

MS ((+)-FAB, m/e (%)) 406 (12, MH$^+$); 338 (15); 150 (25); 131 (100); 103 (40); 56 (75).

Analysis Calculated for $C_{26}H_{31}NO_3$: C, 77.01; H, 7.71; N, 3.45. Found: C, 76.73; H, 7.60; N, 3.38.

EXAMPLE 4

4-[3-(cyclopentyloxy)-4-methoxyphenyl]-1-[(E)-1-oxo-3-(3-pyridinyl)-2-propenyl] piperidine Following the procedure of Example 3, 4-(3-cyclopentyloxy-4-methoxyphenyl)piperidine (1.00 mmol, 0.275 g). trans-3-(3-pyridyl)acrylic acid (1.20 mmol, 0.179 g), 1-(3-dimethylaminopropyl)-3-ethyl carbodiimide (1.20 mmol, 0.230 g) and hydroxybenzotriazole (1.20 mmol, 0.162 g) in CH$_2$Cl$_2$ (30 mL) afforded the amide as a foam. Purification by flash chromatography (SiO$_2$: 75% EtOAc/CH$_2$Cl$_2$) afforded the title compound as a white solid, mp=90°–93° C. (0.320 g, 79%).

$^1$H NMR (DMSO-d$_6$, 400 MHz) δ 8.86 (d, 1H, J=2 Hz); 8.52 (dd, 1H, J=5 Hz, 1.5 Hz); 8.18 (m, 1H); 7.47 (ABq, 2H, J=15 Hz); 7.40 (dd, 1H, J=8 Hz, 5 Hz); 6.83 (d, 1H, J=8 Hz); 6.78 (d, 1H, J=2 Hz); 6.71 (dd, 1H, J=8 Hz, 2 Hz); 4.77 (m, 1H); 4.62 (m, 1H); 4.42 (m, 1H); 3.67 (s, 3H); 3.14 (m, 1H); 2.70 (m, 2H); 1.82 (m, 4H); 1.67 (m, 4H); 1.53 (m, 4 H).

IR (KBr, cm$^{-1}$) 3420 (br), 2940, 2840, 1645, 1600, 1510, 1435, 1245, 1130, 1020, 980, 800, 690, 625.

MS (EI, m/e (%)) 406 (34, M$^+$); 338 (83); 206 (40); 132 (100); 104 (36).

Analysis Calculated for $C_{25}H_{30}N_2O_3$: C, 72.89; H, 7.49; N, 6.80. Found: C, 72.89; H, 7.57; N, 6.52.

EXAMPLE 5

4-[3-(cyclopentyloxy)-4-methoxyphenyl]-N-(2-pyridinylmethyl)-1-piperidinecarboxamide To a magnetically-stirred suspension of 1,1'-carbonyldiimidazole (3.6 mmol, 0.583 g) in dry toluene (20 mL) at 0° C. was added neat 2-(aminomethyl)pyridine (3.6 mmol, 0.371 mL) dropwise over 10 min. The resulting suspension was stirred at room temperature for 30 minutes, then, heated to reflux for 1.25 hours. The oily solution was slowly cooled to room temperature, at which time a solution of 4-(3-cyclopentyloxy-4-methoxyphenyl)piperidine (1.8 mmol, 0.500 g) in toluene (5 mL) was added dropwise over 15 minutes. The resulting suspension was heated to reflux for 4 hours, and the homogenous solution was then cooled to room temperature. The solvent was removed in vacuo, the residue dissolved in EtOAc (200 mL) and washed with 1N NaOH (2×200 mL) and H$_2$O (4×200 mL). The organic layer was dried (Na$_2$SO$_4$) and concentrated in vacuo. The residue was purified by flash chromatography (SiO$_2$: 1) EtOAc: 2) 50% EtOAc/MeOH: 3) MeOH) to afford the title compound as a yellow solid, mp=104°–105° C. (0.3 mmol. 0.121 g. 16% yield).

$^1$HNMR (DMSO-d$_6$, 400 MH) δ8.47 (d, 1H, J=6 Hz); 7.74 (td, 1H, J=8 Hz, 2 Hz); 7.27 (d, 1H, J=8 Hz; 7.22 (dd, 1H, J=7.5 Hz, 2 Hz); 7.15 (t, 1H, J=3 Hz); 6.85 (d, 1H, J=8 Hz); 6.78 (d, 1H, J=2 Hz); 6.72 (dd, 1 H, J=8 Hz, 2 Hz); 4.78 (m, 1H); 4.34 (d, 2H, J=6 Hz); 4.14 (m, 2H); 3.69 (s, 3H); 2.77 (m, 2H); 2.62 (m, 1H); 1.84 (m, 2H); 1.71 (m, 6H); 1.52 (m, 4H). IR (KBr cm$^{-1}$) 3340, 2920, 1620, 1540, 1510, 1250, 1130, 985, 740. MS (DCI, m/e (%) 410 (100, MH$^+$); 135 (24). Analysis Calculated for $C_{24}H_{31}N_3O_3$: C, 70.39; H, 7.63; N, 10.26. Found: C, 69.85; H, 7.55; N, 10.03.

EXAMPLE 6

4-(3-cyclopentylmethyl-4-methoxyphenyl)piperidine-1-carboxylic acid amide

To a stirred solution of 4-(3-cyclopentylmethyl-4-methoxyphenyl)piperidine (1.8 mmol, 0.500 g) in acetic acid (5 mL) was added a solution of sodium cyanate (10.8 mmol, 0.702 g) in water (15 mL) dropwise over 20 minutes at room temperature. The resulting solution was stirred at room temperature overnight, after which the acetic acid was removed in vacuo. The residue was partitioned between EtOAc (200 mL) and H$_2$O (200 mL). The aqueous phase was extracted with EtOAc (1×200 mL), the combined organics dried (Na$_2$SO$_4$), concentrated in vacuo and purified by flash chromatography (SiO$_2$; EtOAc) to give the title compound as a white solid, mp=168°–169° C. (0.5 mmol, 1.054 g, 27%).

$^1$H NMR (DMSO-d$_6$, 400 MHz) δ6.98 (dd, 1H, J=8 Hz, 2 Hz); 6.94 (d, 1H, J=2 Hz); 6.83 d, 1H, J=8 Hz); 5.88 (s, 2H); 4.05 (m, 2H); 3.72 (s, 3H); 2.70 (td, 2H, J=13 Hz, 2 Hz); 2.56 (m, 1H); 2.52 (m, 2H); 2.05 (m, 1H); 1.6 (m, 6H); 1.42 (m, 4H); 1.15 (m, 2H). IR (KBr, cm$^{-1}$) 3400, 3320, 3190, 2940, 2850, 1640, 1590, 1500, 1440, 1390, 1255, 1235, 1100, 1030, 810. MS ((+)-PBCI, m/e (%)) 317 (25, (MH)$^+$); 274 (100); 192 (5). Analysis Calculated for C$_{19}$H$_{28}$N$_2$O$_2$: C, 72.12; H, 8.91; N, 8.85. Found: C, 72.15; H, 9.03; N, 8.71.

EXAMPLE 7

2-[4-(3-cyclopentyloxy-4-methoxyphenyl)piperidin-1-yl]-2-oxo-acetic acid ethyl ester To a stirred solution of 4-(3-cyclopentyloxy-4-methoxyphenyl)piperidine (18.2 mmol, 5.0 g) in dry CH$_2$Cl$_2$ (180 mL) at 0° C. was added neat Et$_3$N (20.0 mmol, 2.8 mL) followed by ethyl oxalyl chloride (20.0 mmol, 2.2 mL) dropwise over 10 minutes. The solution was slowly warmed to room temperature and stirred at room temperature for 2 hours. The reaction mixture was poured into 1N HCl (500 mL) and extracted with CH$_2$Cl$_2$ (2×500 mL). The organics were washed with H$_2$O (3×500 mL), dried (Na$_2$SO$_4$) and concentrated in vacuo to yield an orange syrup. The oil was purified by flash chromatography (SiO$_2$: 1) CH$_2$Cl$_2$, 2) 2% EtOAc/CH$_2$Cl$_2$, 3) 5% EtOAc/CH$_2$Cl$_2$) to afford the title compound as a colorless oil (14.1 mmol, 5.3 g, 78%).

$^1$H NMR (DMSO-d$_6$, 400 MHz) δ6.85 (d, 1H, J=8 Hz); 6.79 (d, 1H, J=2 Hz); 6.71 (dd, 1H, J=8 Hz, 2 Hz); 4.79 (m, 1H); 4.34 (m, 1H); 4.28 (m, 2H); 3.68 (s, 3H); 3.57 (m, 1H); 3.23 (m, 1H); 2.84–2.69 (m, 2H); 1.82 (M, 4H); 1.67 (m, 4H); 1.51 (m, 4H); 1.25 (t, 3H, J=7 Hz). IR (film, cm$^{-1}$); 2940, 2860, 1735, 1655, 1510, 1445, 1250, 1180, 1130, 1100, 1015. MS (DCI, m/e/ (%)) 376 (16, M$^+$); 308 (100); 234 (5).

EXAMPLE 8

2-[4-(3-cyclopentyloxy-4-methoxyphenyl)piperidin-1-yl]-2-oxo-acetic acid

To a stirred solution of 2-[4-(3-cyclopentyloxy-4-methoxyphenyl)piperidin-1-yl]-2-oxo-acetic acid ethyl ester (14.1 mmol, 5.3 g) in THF (140 mL) was added aqueous lithium hydroxide solution (1.0M; 17.6 mmol, 17.6 mL) in one portion at room temperature and the resulting homogeneous solution stirred overnight. The precipitated solution was diluted with H$_2$O (150 mL) and the THF was removed in vacuo. The aqueous phase was diluted with saturated NaHCO$_3$ (400 mL), and acidified with 2N HCl. The aqueous phase was then extracted with EtOAc (3×400 mL) and the combined organic layers were dried (Na$_2$SO$_4$) and concentrated in vacuo. The product was triturated with Et2O/hexane to yield the title compound as a white solid, mp=112°–113° C. (10.8 mmol, 3.74 g, 76%).

$^1$H NMR (DMSO-d$_6$, 400 MHz) δ14.13 (s, 1H); 6.82 (d, 1H, J=8 Hz); 6.78 (d, 1H, J=2 Hz); 6.71 (dd, 1H, J=8 Hz, 2 Hz); 4.78 (m, 1H); 4.34 (m, 1H); 3.70 (s, 3H); 3.62 (m, 1H); 3.22 (m, 1H); 2.74 (m, 2H); 1.80 (m, 4H); 1.66 (m, 4H); 1.50 (m, 4H). IR (KBR, cm$^{-1}$) 3430 (br), 2940, 2860, 1740, 1650, 1600, 1510, 1460, 1440, 1250, 1200, 1130, 1015, 985, 795, 655. MS ((+)-FAB, m/e (%)) 392 (85, (M+2Na-H)$^+$); 370 (85, (M+Na)$^+$); 326 (50); 276 (100); 236 (35); 206(35); 189 (20); 163(45); 150 (58); 137 (65). Analysis Calculated for C$_{19}$H$_{25}$NO$_5$: C, 65.69; H, 7.25; N, 4.03. Found: C, 65.36; H, 7.49; N, 4.01.

EXAMPLE 9

2-[4-(3-cyclopentyloxy-4-methoxyphenyl)piperidin-1-yl]-2-oxo-acetamide

To a magnetically-stirred suspension of 2-[4-(3-cyclopentyloxy-4-methoxyphenyl) piperidin-1-yl]-2-oxo-acetic acid (2.5 mmol, 0.868 g) in dry toluene (25 mL) at room temperature was added oxalyl chloride (2.0M solution in CH$_2$Cl$_2$; 2.75 mmol, 1.38 mL) dropwise over 10 minutes, followed by DMF (4 drops). The resulting homogenous solution was stirred at room temperature for 30 minutes, after which time saturated NH$_3$/CH$_3$CN (25 mL) was added dropwise over 30 minutes. A white solid precipitated out of solution, and the heterogeneous mixture was stirred for 1 hour at room temperature. The solution was diluted with H$_2$O to dissolve the white precipitate and the volatiles were removed in vacuo. The solid was partitioned between saturated NaHCO$_3$ (150 mL) and EtOAc (150 mL) and the aqueous phase was extracted with EtOAc (3×150 mL). The combined organic layers were washed with H$_2$O (300 mL), dried (Na$_2$SO$_4$) and concentrated in vacuo to yield the title compound as a white foam, mp=66°–66.5° C. (1.8 mmol, 0.640 g, 74% yield).

$^1$H NMR (DMSO-d$_6$, 400 MHz) δ8.025 (s, 1H); 7.65 (s, 1H); 6.85 (d, 1H, J=8 Hz); 6.76 (d, 1H, J=2 Hz); 6.70 (dd, 1H, J=8 Hz, 2 Hz); 4.76 (m, 1H); 4.38 (m, 1H); 3.81 (m, 1H); 3.68 (s, 3H); 3.12 (m, 1H); 2.70 (m, 2H); 1.90–1.40 (m, 12H). IR (KBr, cm$^{-1}$) 3360 (br), 2950, 2850, 1690, 1635, 1510, 1270, 1250, 1135. MS (EI, m/e (%)) 346 (45, M$^+$); 278 (85); 234 (50); 205 (100). Analysis Calculated for C$_{19}$H$_{26}$N$_2$O$_4$: C, 65.87; H, 7.56; N, 8.09. Found: C, 65.72; H, 7.47; N, 7.96.

EXAMPLE 10

2-[4-(3-cyclopentyloxy-4-methoxyphenyl)piperidin-1-yl]]-2-oxo-N-pyridin-3-ylmethyl-acetamide In the same manner as Example, 9, 2-[4-(3-cyclopentyloxy-4-methoxyphenyl)piperidin-1-yl]-2-oxo-acetic acid (2.5 mmol, 0.868 g), oxalyl chloride (2.75 mmol, 1.4 mL; 2.0M solution in CH$_2$Cl$_2$), 3-aminomethyl)pyridine (2.5 mmol, 0.25 mL), and pyridine (5.0 mmol, 0.40 mL) afforded the crude product as an oil. For purification, reaction of crude product (700 mg) with maleic acid (1.92 mmol, 0.223 mg) in acetone (5 mL) gave the maleate salt of the compound as a white solid (1.5 mmol), 0.820 g, 59%).

¹H NMR (DMSO-d$_6$, 400 MHz) δ9.28 (t, 1H, J=6 Hz); 8.54 (s, 1H); 8.49 (d, 1H, J=3.7 Hz); 7.75 (m, 1H); 7.43 (dd, 1H, J=8 Hz); 6.84 (d, 1H, J=8 Hz); 6.75 (d, 1H, J=2 Hz); 6.70 (dd, 1H, J=8 Hz, 2 Hz); 6.22 (s, 2H); 4.75 (m, 1H); 4.39 (d, 3H, J=6 Hz); 3.79 (m, 1H); 3.68 (s, 3H); 3.13 (m, 1H); 2.72 (m, 2H); 1.90–1.40 (m, 12H). IR (KBr, cm$^{-1}$) 3320 (br), 2950, 1640, 1510, 1450, 1360, 1250, 1140, 1020, 980, 860, 680. MS ((+)-CI, m/e/ (%)) 554 (20, MH$^+$(salt)); 510 (10); 438 (50, MH$^+$(free base)); 370 (43) 274 (15); 234 (20); 206 (30); 150 (38); 135 (100). Analysis Calculated for C$_{29}$H$_{35}$N$_3$O$_8$: C, 62.92; H, 6.37; N, 7.59. Found: C, 62.84; H, 6.30; N, 6.88.

EXAMPLE 11

2-[4-(3-cyclopentyloxy-4-methoxyphenyl)piperidin-1-yl]-N-hydroxy- 2-oxo-acetamide To a stirred solution of 2-[4-(3-cyclopentyloxy-4-methoxyphenyl)piperidin-1-yl]- 2-oxo-acetic acid ethyl ester (5.3 mmol, 2.0 g) in methanol (55 mL) was added hydroxylamine hydrochloride (21.2 mmol, 1.5 g) followed by potassium hydroxide/methanol solution (5M; 5.3 mL) dropwise at room temperature. A white solid precipitated out of solution as this reaction stirred overnight. The reaction mixture was diluted with H$_2$O (250 mL), acidified with 1N HCl (60 mL) and extracted with EtOAc (2×500 mL). Each organic phase was washed with H$_2$O (250 mL) and the combined organics were dried (Na$_2$SO$_4$) and concentrated in vacuo to give a tan solid. The residue was purified by flash chromatography (SiO$_2$: 1) 80% EtOAc/hexane, 2) EtOAc) to afford the title compound as a white solid, mp=123.5°–124° C. (2.5 mmol, 0.920 g, 48%).

¹H NMR (DMSO-d$_6$, 400 MHz) δ11.2 (s, 1H); 9.29 (m, 1H); 6.86 (d, 1H, J=8 Hz); 6.77 (d, 1H, J=2 Hz); 6.72 (dd, 1H, J=8 Hz, 2 Hz); 4.78 (m, 1H); 4.37 (m, 1H); 3.79 (m, 1H); 3.70 (s, 3H); 3.15 (m, 1H); 2.73 (m, 2H); 1.9–1.4 (m, 12H). IR (KBr, cm$^{-1}$) 3230, 2930, 1680, 1635, 1510, 1440, 1260, 1245, 1225, 1130, 1055, 1030, 1010, 950, 800. MS ((+)-PBCI, m/e (%)) 363 (3, M$^+$); 346 (10); 319 (14); 295 (35); 279 (100); 251 (18); 236 (45); 208 (18); 189 (4); 153 (6). Analysis Calculated for C$_{19}$H$_{26}$N$_2$O$_5$: C, 62.97; H, 7.23; N, 7.73. Found: C, 62.58; H, 7.14; N, 7.63.

EXAMPLE 12

2-[4-(3-cyclopentylmethyl-4-methoxyphenyl)-piperidin-1-yl]-N-hydroxy- 2-oxo-acetamide In the same manner as Example 7, 2-[4-(3-cyclopentylmethyl)- 4-methoxyphenyl)piperidin-1-yl]-2-oxo-acetic acid ethyl ester was prepared from 4-(3-cyclopentylmethyl)-4-methoxyphenyl)piperidine (7.3 mmol, 2.0 g) and ethyl oxalyl chloride (8.0 mmol, 0.808 g) in dry CH$_2$Cl$_2$ (75 mL) as a colorless oil (6.7 mmol, 2.5 g, 92%).

¹H NMR (DMSO-d$_6$, 300 MHz) δ7.00 (m, 2H); 6.80 (m, 1H); 4.27 (m, 3H); 3.71 (s, 3H); 3.55 (m, 1H); 3.18 (m, 1H); 2.75 (m, 2H); 2.48 (m, 2H); 2.05 (m, 1H); 1.79 (m, 2H); 1.65–1.00 (m, 13H).

In the same manner as Example 11, [4-(3-cyclopentylmethyl)-4-methoxyphenyl)piperidin- 1-yl]-2-oxo-acetic acid ethyl ester (2.2 mmol, 0.820 g), hydroxylamine hydrochloride (8.8 mmol, 0.610 g), potassium hydroxide/methanol solution (5M; 2.2 mL) in MeOH (25 mL) afforded a solid which was triturated in ether/hexane to give the title compound as a white solid, mp= 137.5°–138.5° C. (1.9 mmol, 0.676 g, 85%).

¹H NMR (DMSO-d$_6$, 400 MHz) δ11.2 (s, 1H); 9.2 (s, 1H); 7.0 (dd, 1H, J=8 Hz, 2 Hz); 6.96 (d, 1H, J=2 Hz); 6.84 (d, 1H, J=8 Hz); 4.38 (m, 1H); 3.79 (m, 1H); 3.72 (s, 3H); 3.15 (td, 1H, J=13 Hz, 2 Hz); 2.73 (m, 2H); 2.52 (m, 2H); 2.06 (m, 1H); 1.78 (m, 2H); 1.51 (m, 8H); 1.15 (m, 2H). IR (KBr, cm$^{-1}$) 3240 (br); 2940, 2870, 1685, 1645, 1500, 1470, 1450, 1445, 1260, 1245, 1060, 1035, 1010, 955, 850, 815, 710. MS ((–)-FAB, m/e (%)) 359 (40 (M-H)$^-$). Analysis Calculated for C$_{20}$H$_{28}$N$_2$O$_2$: C, 66.64; H, 7.83; N, 7.77. Found: C, 65.33; H, 7.75; N, 7.56.

EXAMPLE 13

2-[4-(3-cyclopentylmethyl-4-methoxyphenyl)-piperidin-1-yl]- 2-oxo-acetamide

In the same manner as Example 8, 2-[4-(3-cyclopentylmethyl- 4-methoxyphenyl)piperidin-1-yl]-2-oxo-acetic acid was prepared from 2-[4-(3-cyclopentylmethyl-4-methoxyphenyl)piperidin- 1-yl]-2-oxo-acetic acid ethyl ester (4.9 mmol, 1.82 g) and aqueous lithium hydroxide (1M, 6.1 mL) in THF (50 mL) as a white solid, mp=99°–101° C. (4.6 mmol, 1.6 g, 94%).

¹H NMR (DMSO-d$_6$, 300 MHz) δ8.50 (br, s, 1H); 7.00 (m, 2H); 6.80 (m, 1H); 4.34 (m, 1H), 3.71 (s, 3H); 3.62 (m, 1H); 3.20 (m, 1H); 2.72 (m, 2H); 2.48 (m, 2H); 2.05 (m, 1H); 1.78 (m, 2H); 1.65–1.35 (m, 8H); 1.13 (m, 2H).

Following the procedure of Example 9, 2-[4-(3-cyclopentylmethyl- 4-methoxyphenyl)piperidin-1-yl]-2-oxo-acetic acid (2.2 mmol, 0.750 g), oxalyl chloride (2.42 mmol, 1.21 mL; 2M solution in CH$_2$Cl$_2$), DMF (4 drops), and saturated NH$_3$/CH$_3$CN (22 mL) in dry toluene (22 mL) afforded a solid which was purified by flash chromatography (SiO$_2$: 40% EtOAc/hexane) to give the title compound as a white solid, mp=117°–118° C. (1.1 mmol, 0.388 g, 51%).

¹H NMR (DMSO-d$_6$, 400 MHz) δ8.05 (s, 1H); 7.63 (s, 1H); 7.0 (dd, 1H, J=8 Hz, 2Hz); 6.69 (d, 1H); J=2 Hz); 6.84 (d, 1H, J=8 Hz); 4.38 (m, 1H); 3.82 (m, 1H); 3.72 (s, 3H); 3.14 (td, 1H, J=13 Hz, 2 Hz); 2.70 (td 2H, J=13 Hz, 2 Hz); 2.51 (m, 2H); 2.06 (m, 1H); 1.75 (m, 2H); 1.52 (m, 8 H); 1.15 (m, 2H). IR (KBr, cm$^{-1}$) 3320, 3170, 2940, 2860, 1695, 1640, 1500, 1460, 1440, 1380, 1260, 1240, 1210, 1145, 1100, 1035, 1010, 815, 635. MS (EI, m/e (%)) 344 (100, M$^+$); 300 (30); 272 (72); 216 (25); 147 (32); 56 (85). Analysis Calculated for C$_{20}$H$_{28}$N$_2$O$_3$: C, 69.74; H, 8.19; N, 8.13. Found: C, 70.10; H, 8.26; N, 8.28.

EXAMPLE 14

3-[4-(3-cyclopentyloxy-4-methoxyphenyl)piperidin-1-yl]-3-oxo-propionic acid methyl ester To a stirred solution of 4-(3-cyclopentyloxy-4-methoxyphenyl)piperidine (40.0 mmol, 11.0 g) in dry CH$_2$Cl$_2$ (400 mL) at 0° C. was added near Et$_3$N (44.0 mmol; 6.1 mL) followed by neat methyl malonyl chloride (44.0 mmol; 4.7 mL) dropwise over 15 minutes. The solution was stirred at 0° for 1 hour and then gradually warmed to room temperature over 3 hours. The reaction mixture was diluted with CH$_2$Cl$_2$ (300 mL) and poured into 1N HCl (700 mL) and partitioned. The aqueous phase was extracted with CH$_2$Cl$_2$ (3×500 mL) and the combined organics were washed with H$_2$O (3×700 mL), dried (Na$_2$SO$_4$), and concentrated in vacuo to afford a brown syrup (13.0 g, 87%) of sufficient purity to be used as such in subsequent transformations.

An analytic sample could be prepared by purification by flash chromatography (SiO$_2$: 1) CH$_2$Cl$_2$; 2) 7% EtOAc/

CH$_2$Cl$_2$; 3) 10% EtOAc/CH$_2$Cl$_2$) followed by trituration in Et$_2$O/hexane to give the title compound as a white solid, mp=78°–79° C.

$^1$H NMR (DMSO-d$_6$, 400 MHz) δ6.85 (d, 1H, J=8 Hz); 6.77 (d, 1H, J=2 Hz); 6.70 (dd, 1H, J=8 Hz, 2 Hz); 4.77 (m, 1H); 4.49 (m, 1H); 3.84 (m, 1H); 3.69 (s, 3H); 3.63 (s, 3H); 3.57 (s, 2H); 3.09 (m, 1H); 2.72–2.57 (m, 2H); 1.88–1.50 (m, 12H). IR (KBr, cm$^{-1}$) 3340 (br), 2904, 2840, 1740, 1650, 1500, 1430, 1330, 1320, 1290, 1260, 1240, 1225, 1210, 1155, 1130, 1100, 1010, 990, 870, 800. MS (PB/(+)-CI, m/e(%)) 376 (100 MH$^+$); 308 (28). Analysis Calculated for C$_{21}$H$_{29}$NO$_5$: C, 67.18; H, 7.78; N, 3.73. Found: C, 66.95; H, 7.62; N, 3.69.

EXAMPLE 15

3-[4-(3-cyclopentyloxy-4-methoxyphenyl)piperidin-1-yl]-3-oxo-propionic acid

In the same manner as Example, 8, 3-[4-(3-cyclopentyloxy- 4-methoxyphenyl)piperidin-1-yl]-3-oxo-propionic acid methyl ester (6.7 mmol, 2.5 g), aqueous lithium hydroxide (1.0M; 8.4 mmol, 8.4 mL) in THF (70 mL) afforded the title compound as an off-white solid, mp=122°–123° C. (6.0 mmol, 2.16 g, 89%).

$^1$H NMR (DMSO-d$_6$, 400 MHz) δ12.64 (s, 1H); 6.85 (d, 1H, J=2 Hz); 6.70 (dd, 1H, J=8 Hz, 2 Hz); 4.76 (m, 1H); 4.50 (m, 1H); 3.86 (m, 1H); 3.69 (s, 3H); 3.44 (ABq, 2H, J=16 Hz); 3.08 (td, 1H, J=13 Hz, 2 Hz); 2.64 (m, 2H); 1.9–1.34 (m, 12H). IR (KBR, cm$^{-1}$) 3420 (br), 2940, 2910, 2700, 2530, 1725, 1585, 1510, 1500, 1450, 1435, 1370, 1240, 1225, 1135, 1030, 990, 955, 870, 810, 620. MS ((+)-PBCI, m/e (%)) 362 (4, MH$^+$); 318 (100); 294 (10); 250 (35). Analysis Calculated for C$_{20}$H$_{27}$NO$_5$: C, 66.46; H, 7.53; N, 3.88. Found: C, 66.39; H, 7.50; N, 4.15.

EXAMPLE 16

3-[4-(3-cyclopentyloxy-4-methoxyphenyl)piperidin-1-yl]-3-oxo-propionamide

In the same manner as Example, 9, 3-[4-(3-cyclopentyloxy- 4-methoxyphenyl)piperidin-1-yl]-3-oxo-propionic acid (0.70 mmol, 0.25 g), oxalyl chloride (0.77 mmol, 0.385 mL; 2M solution in CH$_2$Cl$_2$), DMF (4 drops) and saturated NH$_3$/CH$_3$CN solution (10 mL) in dry toluene (10 mL) afforded a solid which was triturated in Et$_2$O/hexane to give the title compound as a white solid, mp=132°–133° C. (0.40 mmol, 0.150 g, 60%).

$^1$H NMR (DMSO-d$_6$, 400 MHz) δ7.42 (s, 1H); 6.97 (s, 1H); 6.85 (d, 1H, J=8 Hz); 6.77 (d, 1H, J=2 Hz); 6.70 (dd, 1H, J=8 Hz, 2 Hz); 4.76 (m, 1H); 4.50 (m, 1H); 3.93 (m, 1H); 3.69 (s, 3H); 3.27 (ABq, 2H, J=15 Hz) 3.06 (m, 1H); 2.72–2.54 (m, 2H); 1.90–1.32 (m, 12H). IR (KBr, cm$^{-1}$) 3340, 3170, 2920, 2860, 1665, 1620, 1500, 1445, 1325, 1240, 1160, 1130, 1100, 1020, 985, 870, 800, 760. MS (EI, m/e (%)) 360 (10, M$^+$); 292 (29); 275 (15); 234 (9); 206 (100); 190 (25); 150 (38); 103 (25). Analysis Calculated for C$_{20}$H$_{28}$N$_2$O$_4$: C, 66.64; H, 7.83; N, 7.77. Found: C, 66.13; H, 7.82; N, 7.40.

EXAMPLE 17

3-[4-(3-cyclopentyloxy-4-methoxyphenyl)piperidin-1-yl]- 2-(hydroxyimino)-3-oxo-propionic acid methyl ester To 3-[4-(3-cyclopentyloxy-4-methoxyphenyl)-piperidin-1-yl]- 3-oxo-propionic acid methyl ester (5.3 mmol, 2.0 g) was added a solution of HCl/Et$_2$O (1N, 55 mL) and isoamyl nitrite (6.36 mmol, 0.854 mL) at room temperature. After 10 minutes, the reaction mixture had become homogenous, and a white precipitate formed after and additional 30 minutes. After 3 hours, the reaction mixture was diluted with EtOAc and washed with H$_2$O. The aqueous phase was extracted with EtOAc, the organics dried (Na$_2$SO$_4$) and concentrated in vacuo. The residue was triturated in Et$_2$O/hexane to yield the title compound as a white solid, mp=159°–160° C. (4.7 mmol, 1.89 g, 88%).

$^1$H NMR (DMSO-d$_6$, 400 MHz) δ12.90 (s, 1H); 6.86 (d, 1H, J=8 Hz); 6.75 (d, 1H, J=2 Hz); 6.69 (dd, 1H, J=8 Hz, 2 Hz); 4.76 (m, 1H); 4.47 (m, 1H); 3.78 (s, 3H); 3.69 (s, 3H); 3.43 (m, 1H); 3.15 (m, 1H); 2.75 (m, 2H); 1.90–1.40 (m, 1–2H). IR (KBr, cm$^{-1}$) 3390 (br), 3140 (br), 2940, 2850, 1745, 1590, 1510, 1450, 1440, 1370, 1280, 1260, 1250, 1230, 1135, 1025. MS (DEI, m/e (%)) 404 (30, M$^+$); 388 (17); 336 (24); 319 (27); 287 (74); 260 (48); 206 (50); 189 (100); 163 (35); 144 (85); 131 (34). Analysis Calculated for C$_{21}$H$_{28}$N$_2$O$_6$: C, 62.36; H, 6.98; N, 6.93. Found: C, 62.30; H, 6.98; N, 6.87.

EXAMPLE 18

3-[4-(3-cyclopentyloxy-4-methoxyphenyl)piperidin-1-yl]-N-hydroxy-2-(hydroxyimino)-3-oxo-propionamide In the same manner as Example 11, 3-[4-(3-cyclopentyloxy-4-methoxyphenyl)piperidin- 1-yl]-2-(hydroxyimino)-3-oxo-propionic acid methyl ester (0.6 mmol, 0.250 g), hydroxylamine hydrochloride (2.4 mmol, 0.167 g), potassium hydroxide/methanol solution (5M; 0.6 mL) in MeOH (6 mL) gave a solid which was recrystallized from EtOAc/hexane to afford the title compound as a white solid, mp=119°–121° C. (0.3 mmol, 0.135 g, 55%).

$^1$H NMR (DMSO-d$_6$, 400 MHz) δ12.10 (s, 1H); 11.08 (s, 1H); 9.12 (s, 1H); 6.86 (d, 1H, J=8 Hz); 6.74 (d, 1H, J=2 Hz); 6.69 (dd, 1H, J=8 Hz, 2 Hz); 4.77 (m, 1H); 4.46 (m, 1H); 3.69 (s, 3H); 3.49 (m, 1H); 3.14 (m, 1H); 2.74 (m, 2H); 1.9–1.36 (m, 12H). IR (KBr, cm$^{-1}$) 3200 (br), 2940, 2860, 1660, 1610, 1510, 1440, 1370, 1265, 1250, 1150, 1130, 1010, 845. MS ((+)-PBCI, m/e (%)) 406 (2, M$^+$); 338 (10); 306 (20); 261 (100); 234 (28); 208 (13). Analysis Calculated for C$_{20}$H$_{27}$N$_3$O$_6$.0.2 EtOAc: C, 59.25; H, 6.71; N, 10.36. Found: C, 58.99; H, 6.76; N, 9.93.

EXAMPLE 19

(E)-3-[4-(3-cyclopentyloxy-4-methoxyphenyl)piperidin-1-yl]-2-(hydroxyimino)-3-oxo-propionamide In the same manner as Example 17, 3-[4-(3-cyclopentyloxy- 4-methoxyphenyl)piperidin-1-yl]-3-oxo-propionamide (2.1 mmol, 0.740 g), HCl/Et$_2$O (35 mL), and isoamyl nitrite (2.52 mmol, 0.339 mL) afforded a tan solid which was triturated in Et$_2$O/hexane to give the title compound as a white solid, mp≦109°–111° C. (1.8 mmol, 0.701 g, 86%).

$^1$H NMR (DMSO-d$_6$, 400 MHz) δ12.12 (s, 1H); 7.52 (s, 1H); 7.43 (s, 1H); 6.85 (d, 1H); J=8 Hz); 6.74 (d, 1H); J=2 Hz); 6.68 (dd, 1H, J=8 Hz, 2 Hz); 4.74 (m, 1H); 4.45 (m, 1H); 3.69 (s, 3H); 3.41 (m, 1H); 3.12 (m, 1H); 2.73 (m, 2H); 1.9–1.37 (m, 12H). IR (KBr, cm$^{-1}$) 3320 (br), 2940, 2850, 1680, 1620, 1510, 1440, 1365, 1270, 1250, 1220, 1130, 1000. MS (EI, m/e (%)) 389 (10, M$^+$); 328 (18); 287 (24); 260 (100); 100); 186 (38); 126 (28). Analysis Calculated for C$_{20}$H$_{27}$N$_3$O$_5$: C, 61.68; H, 6.99; N, 10.79. Found: C, 61.08; H, 6.96; N, 10.58.

EXAMPLE 20

3-[4-(3-cyclopentyloxy-4-methoxyphenyl)piperidin-1-yl]-2-hydroxyimino)-3-oxo-propionic acid In the same manner as Example, 8, 3-[4-(3-cyclopentyloxy- 4-methoxyphenyl)piperidin-1-yl]-2-(hydroxyimino)-3-oxo-propionic acid methyl ester (0.87 mmol, 0.350 g), aqueous lithium hydroxide (1M; 2.17 mmol, 2.2 mL) in THF (10 mL) afforded the title compound as a white solid, mp=121°–122° C. (0.7 mmol, 0.291 g, 86%).

$^1$H NMR (DMSO-$d_6$, 400 MHz) δ13.45 (s, 1H); 12.61 (s, 1H); 6.85 (d, 1H, J=8 Hz); 6.74 (d, 1H, J=2 Hz); 6.68 (dd, 1H, J=8 Hz, 2 Hz); 4.75 (m, 1H); 4.45 (m, 1H); 3.69 (s, 3H); 3.43 (m, 1H); 3.14 (m, 1H); 2.74 (m, 2H); 1.9–1.36 (m, 12H). IR (KBr, cm$^{-1}$) 3340, 2930, 2850, 1690, 1590, 1510, 1440, 1370, 1270, 1250, 1220, 1130, 1005, 985. MS ((–)-FAB, m/e (%)) 389 (90, (M-H)$^-$); 373 (100) 345 (90) 318 (50); 259 (40); 206 (20); 148 (90). Analysis Calculated for $C_{20}H_{26}N_2O_6$: C, 61.53; H, 6.71; N, 7.18. Found: C, 61.57; H, 6.71; N, 7.01.

EXAMPLE 21

3-[4-(3-Cyclopentyloxy-4-methoxy-phenyl)-piperidin-1-yl]-4-isopropoxy-cyclobut-3-ene-1,2-dione To a stirred solution of the piperidine (1.8 mmol, 0.5 g) in dry THF (10 mL) at room temperature was added a solution of the 3,4-diisopropoxy-3-cyclobutyene-1,2-dione (1.8 mmol, 0.357 g) in dry THF (10 mL). The solution was stirred at room temperature for 24 hours. The THF was removed in vacuo and the residue partitioned between H$_2$O (100 mL) and EtOAc (100 mL). The aqueous layer was extracted again with one 100 mL portion of EtOAc and the combined organics dried over Na$_2$SO$_4$. The crude product was purified via column chromatography (SiO$_2$: 40% EtOAc/hexane) to afford a white solid (1.0 mmol. 0.420 g, 56%).

$^1$H NMR (DMSO-$d_6$, 400 MHz) δ6.82 (d, 1H); 6.70 (dd, J=8.3; 2.1 Hz, 1H); 5.26 (m, 1H); 4.77 (m, 1H); 4.53 (m, 1H); 3.99 (m, 1H); 3.69 (s, 3H); 3.25 (m, 2H); 2.72 (m, 1H); 1.70 (m, 12H); 1.38 (m, 6H). IR (KBR (cm$^{-1}$)) 3445, 2930, 2870, 1800, 1705, 1600, 1515, 1440, 1270, 1135, 1100. MS (EI, m/e (%)) 413 (70, M$^+$), 345 (14), 303 (100), 247 (47), 219 (57). Anal. calc'd for $C_{24}H_{31}NO_5$: C, 69.71; H, 7.56; N, 3.39. Found: C, 69.59; H, 7.59; N, 3.27.

EXAMPLE 22

3-[4-(3-Cyclopentyloxy-4-methoxy-phenyl)-piperidin-1-yl]-4-hydroxy-cyclobut-3-ene-1,2-dione To a stirred solution of 3-[4-(3-cyclopentyloxy- 4-methoxy-phenyl)piperidin-1-yl]-4-isopropoxy-cyclobut-3-ene-1,2-dione (0.4 mmol, 0.166 g) in THF (5 mL) was added lithium hydroxide solution (1.0M, 0.500 mL) neat in one portion. The solution continued to stir at room temperature for 24 hours. The reaction was then diluted with H$_2$O (5 mL) and the THF removed in vacuo. The aqueous solution was diluted with saturated aqueous NaHCO$_3$ (50 mL) and then acidified with 1.0N HCl. The acidic solution was extracted with EtOAc (2×100 mL) and the organics dried over Na$_2$SO$_4$ and concentrated to an oil. The oil was triturated in Et$_2$O/hexane to yield a yellow powder (0.1 mmol, 0.050 g, 34%).

$^1$H NMR (DMSO-$d_6$, 400 MHz) δ6.82 (d, 1H); 6.81 (d, 1H); 6.77 (dd, J=8.1:1.87 Hz, 1H); 4.78 (m, 1H); 4.34 (m, 2H); 3.68 (s, 3H); 3.22 (td, J=12 Hz, 2 Hz, 2H); 2.71 (m, 1H); 1.75 (m, 10H); 1.55 (m, 2H). IR (KBr (cm$^{-1}$)) 3430, 2940, 1810, 1685, 1590, 1515, 1495, 1460, 1265, 1140, 985. MS (EI, m/e (%)) 371 (10, M$^+$), 303 (38), 207 (17), 67 (100). Anal. Calc'd for $C_{21}H_{25}NH_5$: C, 67.90; H, 6.78; N, 3.77. Found: C, 68.06; H, 7.03; N, 3.67.

EXAMPLE 23

3-[4-(3-Cyclopentyloxy-4-methoxy-phenyl)-piperidin-1-yl]-4-hydroxyamino-cyclobut-3-ene-1,2-dione To a stirred solution of 3-[4-(3-cyclopentyloxy-4-methoxy-phenyl)-piperidin- 1-yl]-4-isopropoxy-cyclobut-3-ene-1,2-dione (6.8 mmol, 2.8 g) in dry MeOH (70 mL) was added hydroxylamine.HCl (27.2 mmol, 1.99 g) in one portion, followed by a solution of potassium hydroxide in methanol (5.0M, 6.8 mL) dropwise. A precipitate starts to form at this addition. The reaction stirred at room temperature for 3 hours, and, at that time, TLC analysis shows reaction to be about 95% complete. The reaction mixture was diluted with H$_2$O (250 mL) and acidified with 1.0N HCl. The acidic solution was extracted with EtOAc (2×250 mL) and organic extracts dried over Na$_2$SO$_4$. The filtrate was concentrated to a red solid. The solid was triturated in CH$_2$Cl$_2$/hexane to afford a red solid (5.4 mmol, 2.1 g, 79%).

$^1$H NMR (DMSO-$d_6$, 400 MHz) δ10.57 (s, 1H); 9.79 (s, 1H); 6.83 (dd, J=8.3;1.87 Hz, 2H); 6.72 (dd, J=1.87; 2.08 Hz, 1H); 4.79 (m, 1H); 4.47 (br s, 2H); 3.69 (s, 3H); 3.19 (m, 2H); 2.71 (m, 1H); 1.70 (m, 12H). IR (KBr (cm$^{-1}$)) 3400, 3160, 2930, 2850, 1780, 1655, 1570, 1500, 1255, 1135, 985. MS (+FAB, m/e (%)) 371 (17, M-H$_2$O; +2H), 303 (78), 276 (100). Anal. calc'd for $C_{21}H_{26}N_2O_5$: C, 65.26; H, 6.78; N, 7.24. Found: C, 65.14; H, 6.88; N, 7.16.

EXAMPLE 24

2-[4-(3-Cyclopentylidenemethyl-4-methoxy-phenyl)-piperidin- 1-yl]-oxo-acetic acid ethyl ester To a stirred solution of the piperidine (4.6 mmol, 1.3 g) in dry CH$_2$Cl$_2$ (50 mL) at 0° C. was added neat Et$_3$N (5.1 mmol, 710 µL), followed by ethyloxalyl chloride (5.1 mmol, 570 µL) dropwise. The solution slowly warmed and stirred at room temperature for 1.5 hours at which time TLC shows no starting material left. The reaction was diluted with CH$_2$Cl$_2$, then poured into 1N HCl (300 mL) and extracted with CH$_2$Cl$_2$ (2×200 mL). The organics were washed with H$_2$O (2×250 mL), dried Na$_2$SO$_4$) and concentrated in vacuo to an oil (1.76 g). The oil was purified via flash chromatography (SiO$_2$: CH$_2$Cl$_2$) to afford a colorless oil (4.1 mmol, 1.53 g, 90%).

$^1$H NMR (DMSO-$d_6$, 300 MHz) δ7.15 (d, 1H); 7.04 (dd, J=8.5; 2.0 Hz, 1H); 6.87 (d, 1H); 6.46 (m, 1H); 4.38 (m, 1H); 4.29 (q, 3H); 3.72 (s, 3H); 3.59 (m, 1H); 3.23 (m, 1H); 2.80 (m, 2H); 2.41 (m, 4H); 1.84 (d, 2H); 1.55 (m, 4H); 1.27 (t, 3H).

EXAMPLE 25

2-[4-(3-Cyclopentylidenemethyl-4-methoxy-phenyl)-piperidin- 1-yl]-N-hydroxy-2-oxo-acetamide To a stirred solution of 2-[4-(3-cyclopentylidenemethyl-4-methoxy-phenyl)-piperidin-1-yl]-oxo-acetic acid ethyl ester (0.4 mmol, 0.150 g) in methanol (5 mL) was added hydroxylamine.HCl (1.6 mmol, 0.111 g), followed by potassium hydroxide/methanol solution (5 M solution; 0.4 mL) dropwise at room temperature. A white solid precipitated out of solution as this reaction stirred for 3 hours. The reaction went to completion as seen by TLC. The reaction mixture was diluted with $H_2O$ (100 mL), acidified with 1N HCl and extracted with EtOAc (3×100 mL). Each organic phase was washed with $H_2O$ (1×50 mL) and the combined organics were dried ($Na_2SO_4$) and concentrated in vacuo to a white solid. The solid was triturated in $Et_2O$/hexane to afford pure white crystals which were dried overnight at 45° C. to give the title compound, mp 127°–128° C. (0.3 mmol, 0.017 g, 75%).

$^1H$ NMR (DMSO-$d_6$, 400 MHz) δ11.25 (s, 1H), 9.20 (s, 1H); 7.13 (d, 1H); 7.02 (dd, J=8.5; 2.0 Hz, 1H); 6.87 (d, 1H); 6.46 (m, 1H); 4.38 (m, 1H); 3.80 (m, 1H); 3.71 (s, 3H); 3.16 (m, 1H); 2.74 (m, 2H); 2.41 (m, 4H); 1.80 (m, 2H); 1.58 (m, 6H). IR (KBr, (cm$^{-1}$)) 3240, 2930, 1685, 1630, 1490, 1445, 1260, 1235, 1025, 1000, 805. MS (+FAB, m/e(%)) 359 (90, [M+H]$^+$), 358 (85, M$^+$), 298 (30), 270 (50), 253 (25), 227 (28). Anal. Calc'd for $C_{20}H_{26}N_2O_2$: C, 67.02; H, 7.31; N, 7.81. Found: C, 66.68; H, 7.26; N, 7.85.

EXAMPLE 26

[4-(3-Cyclopentylidenemethyl-4-methoxy-phenyl)-piperidin-1-yl]-oxo-acetic acid solution salt hydrate To a stirred solution of 2-[4-(3-cyclopentylidenemethyl-4-methoxy-phenyl)-piperidin-1-yl]-oxo-acetic acid ethyl ester (1.7 mmol, 0.62 g) in THF (17 mL), aqueous lithium hydroxide solution (1.0M, 2.1 mL) was added in one portion at room temperature and the resulting homogeneous solution stirred overnight. The reaction mixture was diluted with $H_2O$ (10 mL) and the THF removed in vacuo. The aqueous phase was diluted with saturated aqueous $NaHCO_3$ (150 mL), and then the basic solution was acidified with 1N HCl. The aqueous phase was then extracted with EtOAc (2×300 mL) and the combined organic layers were dried ($Na_2SO_4$) and concentrated in vacuo to a yellow solid. The solid was purified by column chromatography ($SiO_2$: 10% MeOH/$CH_2Cl_2$) and crystallization with $CH_2Cl_2$/$Et_2O$ to yield a light yellow solid which was dried overnight at 45° C. to afford the title compound (0.9 mmol, 0.313 g, 51%).

$^1H$ NMR (DMSO-$d_6$, 400 MHz) δ7.11 (d, 1H); 7.01 (dd, J=8.5; 2.0 Hz, 1H); 6.86 (d, 1H); 6.47 (m, 1H); 4.38 (m, 1H); 4.01 (br s, 1H); 3.71 (s, 3H); 3.02 (t, 1H); 2.69 (t, 1H); 2.58 (t, 1H); 2.40 (m, 4H); 1.65 (m, 6H); 1.42 (m, 2H). IR (KBr, (cm$^{-1}$)) 3400, 2930, 2855, 1600, 1490, 1450, 1370, 1260, 1240, 1010. MS (−FAB, m/e (%)) 342 (85, [M−H]$^-$), 297 (100), 192 (10), 175 (20), 148 (100). Anal. calc'd for $C_{20}H_{25}NO_4Na$: C, 62.65; H, 6.84; N, 3.65. Found: C, 62.84; H, 6.66; N, 4.21.

EXAMPLE 27

2-[4-(3-Cyclopentylidenemethyl-4-methoxy-phenyl)-piperidin-1-yl]-2-oxo-acetamide To a magnetically stirred suspension of [4-(3-cyclopentylidenemethyl-4-methoxy-phenyl)piperidin-1-yl]-oxo-acetic acid (1.2 mmol, 0.40 g) in dry toluene (15 mL) at room temperature was added oxalyl chloride (2.0M in $CH_2Cl_2$; 1.3 mmol, 0.65 mL) dropwise over 10 minutes, followed by DMF (3 drops) to promote gas evolution. The resulting homogeneous solution stirred at room temperature for 45 minutes, at which time saturated $NH_3$/$CH_3CN$ (15 mL) was added dropwise over 15 minutes. A white solid precipitated out of solution as the mixture was stirred for another ¾ hour. At that time, TLC analysis shows reaction to be complete.

The solution was diluted with $H_2O$ to dissolve the white precipitate and then the THF was removed in vacuo. The aqueous phase was diluted with saturated aqueous $NaHCO_3$ solution (100 mL) and then extracted with EtOAc (2×200 mL). Each organic phase was washed with $H_2O$ (1×100 mL) and then the combined organics were dried ($Na_2SO_4$) and concentrated to yield a white solid. This compound was purified via column chromatography ($SiO_2$: 40% EtOAc/hex) to afford a pure white solid of the title compound as a pure white solid, mp 116°–117° C. (0.7 mmol, 0.231 g, 56%).

$^1H$ NMR (DMSO-$d_6$, 400 MHz) δ8.16 (s, 1H); 7.63 (s, 1H); 7.14 (d, 1H); 7.02 (dd, J=8.5; 2.0 Hz, 1H); 6.88 (d, 1H); 6.48 (m, 1H); 4.39 (m, 1H); 3.83 (m, 1H); 3.72 (s, 3H); 3.15 (m, 1H); 2.72 (m, 2H); 2.41 (m, 4H); 1.79 (m, 2H); 1.57 (m, 6H). IR (KBr (cm$^{-1}$)) 3310, 3170, 2940, 1695, 1650, 1490, 1460, 1380, 1265, 1245, 1210, 1115, 1030, 1015, 815, 635. MS (+FAB, m/e (%)) 342 (100, [M]$^+$), 298 (25), 270 (35). Anal. Calc'd for $C_{20}H_{26}N_2O_3$. C, 70.15; H, 7.65; N, 8.18. Found: C, 69.82; H, 7.66; N, 8.10.

EXAMPLE 28

2-[4-(3-Cycloheptylidenemethyl-4-methoxyphenyl)-piperidin-1-yl]-oxo-acetic acid ethyl ester To a stirred solution of the piperidine (6.3 mmol, 1.9 g) in dry $CH_2Cl_2$ (65 mL) at 0° C. was added neat $Et_3N$ (7.0 mmol, 974 μL) followed by ethyloxalychloride (7.0 mmol, 780 μL) dropwise. The solution slowly warmed and stirred at room temperature for 2 hours, at which time, TLC shows reaction to be complete. The mixture was diluted with $CH_2Cl_2$, poured into 1N HCl, and then extracted with $CH_2Cl_2$ (2×200 mL). The organic were washed with $H_2O$ 1×300 mL), dried ($Na_2SO_4$) and concentrated to a yellow oil. The crude product was purified via column chromatography ($SiO_2$: $CH_2Cl_2$) to afford a colorless oil (5.5 mmol, 2.2 g, 87%).

$^1H$ NMR (DMSO-$d_6$, 300 MHz) δ7.11 (dd, J=22.8; 6.0 Hz, 1H); 7.03 (d, 1H); 6.92 (d, 1H); 6.29 (s, 1H); 4.43 (m, 1H); 4.32 (q, 2H); 3.76 (s, 3H); 3.62 (d, 1H); 3.30 (t, 1H); 2.84 (m, 2H); 2.38 (m, 4H); 1.88 (d, 2H); 1.61 (m, 10H); 1.32 (t, 3H).

EXAMPLE 29

2-[4-(3-Cycloheptylidenemethyl-4-methoxyphenyl)-piperidin-1-yl]-N-hydroxy-2-oxo-acetamide To a stirred solution of 2-[4-(3-cycloheptylidenemethyl-4-methoxy-phenyl)-piperidin-1-yl]-oxo-acetic acid ethyl ester (0.6 mmol, 0.250 g) in methanol (5 mL) was added hydroxylamine.HCl (2.4 mmol, 0.167 g, followed by KOH/MeOH solution (5M, 600 μL) dropwise at room temperature. A white solid precipitated out of solution at this reaction continued to stir overnight at room temperature. The reaction went to completion as seen by TLC. The reaction mixture was diluted with $H_2O$ (150 mL), acidified with 1N HCl and then extracted with EtOAc (3×100 mL). Each organic phase was washed with $H_2O$ (1×100 mL) and the combined organics were dried ($Na_2SO_4$) and concentrated to yield a white solid. The solid was triturated in $Et_2O$/hexane to afford the pure title compound, mp 135°–136° C. (0.3 mmol, 0.125 g, 54%).

$^1H$ NMR (DMSO-$d_6$, 400 MHz) δ11.20 (s, 1H); 9.20 (s, 1H); 7.05 (dd, J=8.5; 2.0 Hz, 1H); 6.98 (d, 1H); 6.89 (d, 1H);

6.22 (s, 1H); 4.38 (d, 1H); 3.79 (d, 1H); 3.71 (s, 3H); 3.17 (t, 1H); 2.74 (t, 2H); 2.43 (m, 4H); 1.80 (m, 2H); 1.55 (m, 10H). IR (KBr, (cm$^{-1}$)) 3430 (br), 3180, 2930, 1675, 1615, 1495, 1445, 1370, 1250, 1035, 815. MS (–FAB, m/e (%)) 385 (94, [M-H]$^-$), 369 (8), 297 (100), 256 (6), 192 (15), 175 (25), 148 (100). Anal. calc'd for $C_{22}H_{30}N_2O_4$. C, 68.37; H, 7.82; N, 7.25. Found: C, 67.03; H, 7.62; N, 7.02.

EXAMPLE 30

2-[4-(3-Cycloheptylidenemethyl-4-methoxy-phenyl)-piperidin-1-yl]-oxo-acetic acid To a stirred solution of 2-[4-(3-cycloheptylidenemethyl-4-methoxy-phenyl)-piperidin-1-yl]-oxo-acetic acid ethyl ester (2.8 mmol, 1.12 g) in THF (30 mL), aqueous lithium hydroxide solution (1.0M, 3.5 mL) was added in one portion at room temperature and the resulting homogeneous solution stirred overnight. The reaction mixture was diluted with H$_2$O (30 mL) and the THF removed in vacuo. The aqueous phase was diluted with saturated aqueous NaHCO$_3$ solution (200 mL), then acidified with 1N HCl and then extracted with EtOAc (3×200 mL). Each organic layer was washed with H$_2$O (1×100 mL) and the combined organics were dried (Na$_2$SO$_4$) and concentrated to a white solid. The solid was crystallized in Et$_2$O/hexane to yield a white solid which was dried in vacuo ~45° C. mp 121°–122° C. (2.4 mmol, 0.887 g, 85%).

$^1$H NMR (DMSO-d$_6$, 400 MHz) δ14.10 (br s, 1H); 7.06 (dd, J=8.5; 2.0 Hz, 1H); 6.98 d, 1H); 6.88 (d, 1H); 6.22 (s, 1H); 4.36 (m, 1H); 3.71 (s, 3H); 3.62 (m, 1H); 3.23 (m, 1H); 2.76 (m, 2H); 2.34 (m, 4H); 1.82 (d, 2H); 1.52 (m, 10H). IR (KBr, (cm$^{-1}$)) 3500, 2930, 2860, 1745, 1710, 1625, 1495, 1380, 1250, 1025, 820. MS (DEI, m/e (%)) 371 (20, M$^+$), 328 (18), 327 (63), 233 (40), 232 (100). Anal. calc'd for $C_{22}H_{29}NO_2$: C, 71.13; H, 7.87; N, 3.77. Found: C, 68.87; H, 7.93; N, 3.67.

PHARMACOLOGY

A solution containing PDE IV is prepared from canine tracheal muscle as follows: The dog is euthanized with an overdose of Beuthanasia® while under anesthesia induced by a 33 mg/kg IV bolus of Nembutal. The trachealis muscle is removed, cleaned of connective tissue, and minced thoroughly. Three to four grams of tissue is the homogenized in Tris-HCl buffer (pH 7.8) using a Polytron. The homogenate is then centrifuged at 25,000 x g (4° C.) for 30 minutes. The supernatant is decanted and filtered through four layers of gauze, and applied to a 40 cm×2 cm DEAE-Sepharose column that is equilibrated with Tris-HCl buffer (pH 7.8). The column is then washed with an additional 240 mL of buffer to remove unbound proteins. PDE is eluted using 450 mL of Tris-HCl buffer containing a linear gradient of 0.0–1.0M sodium acetate (80 mL/hr), and 7.5 mL fractions are collected. Each fraction is assayed for cAMP- and cGMP-metabolizing PDE activity. Fractions eluting at approximately 0.6M sodium acetate, and containing cAMP but not cGMP metabolic activity are pooled and used as a PDE stock solution for assaying PDE IV inhibitory activity.

PDE IV activity is assayed as described previously [See Thompson et al., Advances in Cyclic Nucleotide Research, 10, 69 (1979)] at 30° C. in a reaction mixture containing: 10 mM Tris-HCl (pH 7.8), 5 mM MgCl$_2$, 1 mM β-mercaptoethanol, 1 μM $^3$H-cAMP, 10 μM CI-930(5-methyl-4-(4-imidazol-1-ylphenyl)-4,5-dihydro-3(2H)pyridazone), PDE IV stock solution, and the desired concentration of test compound. CI-930 is included as an inhibitor of the cyclic GMP-sensitive, cyclic AMP-selective PDE (PDE III) that is also present in the PDE IV stock solution when prepared as described above. The ability of a test compound to inhibit PDE IV is determined by measuring the reduction in cAMP metabolism produced by the test compound and expression it as a percentage of the reduction induced by 10 μM rolipram, a potent inhibitor of PDE IV [see Beavo, Advances in Second Messenger and Phosphoprotein Research, 22, 1 (1988)]. IC$_{50}$s are calculated for each test compound as the concentration of test compound that inhibits PDE IV by 50%. The IC$_{50}$s for the compounds of Examples 1 to 30 range from about 10 nM to about 6 μM.

PHARMACEUTICAL COMPOSITION AND ADMINISTRATION

When the compounds of the invention are employed in the treatment of acute or chronic bronchial asthma, then can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carobxymethylcellulose, low melting wax, cocoa butter and the like. Diluents, flavoring agents, solubilizers, lubricants, suspending agents, binders, tablet-disintegrating agents and the like may be employed. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be formulated into dry aerosol inhalation formulations.

The dosage requirements vary with the particular compositions employed, the route of administration, the severity of the symptoms presented and the particular subject being treated. Treatment will generally be inititated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times throughout the day. The contemplated dosage is from 0.001 to 100 mg/kg/day, preferably from 0.001 to 50 mg/kg/day.

What is claimed is:

1. A compound which has the formula:

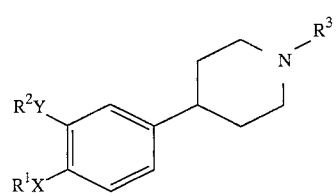

where:

R$^1$=H, C$_1$–C$_6$ alkyl;

R$^2$=C$_3$–C$_7$ alkyl, C$_3$–C$_7$ cycloalkyl or, C$_4$–C$_8$ cycloalkylidene when Y is CH;

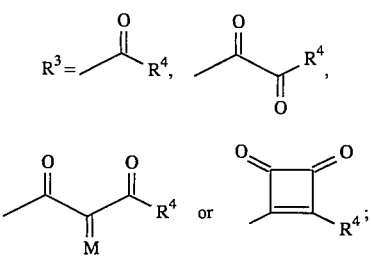

$R^4$=H, $OR^5$, $NHR^5$, NHOH, $NHNH_2$ or

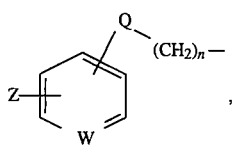

with a proviso that when $R^3$ is —$COR^4$, then $R^4$ cannot be

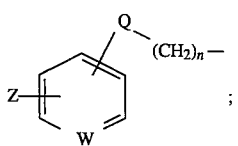

$R^5$=H, $C_1$–$C_6$ alkyl, $C_3$–$C_8$ cycloalkyl, aryl, substituted aryl, aralkyl, substituted aralkyl or

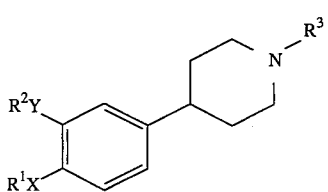

W=N or CH;
X=$CH_2$, O, S, or NH;
Y=$CH_2$, CH, O, S, or NH;
Q=a bond or CH=CH;
n=0, 1 2, 3, or 4;
M=O, NOH or $H_2$;
Z=H or halogen;
or a pharmaceutically acceptable salt thereof.

2. A compound of claim 1 having the formula

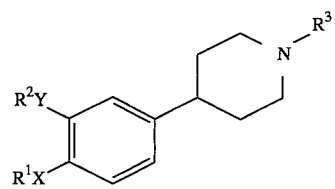

where:
$R^1$=H, $C_1$–$C_3$ alkyl;
$R^2$=$C_4$–$C_6$ alkyl, $C_5$–$C_6$ cycloalkyl or $C_4$–$C_8$ cycloalkylidene when Y is CH;

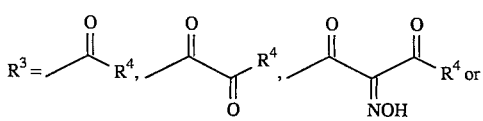

$R^4$=$OR^5$, $NHR^5$, or NHOH;
$R^5$=H, $C_1$–$C_6$ alkyl, aralkyl or

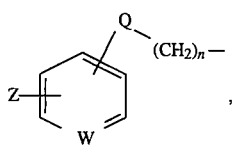;

W=N or CH;
X=$CH_2$ or O;
Y=$CH_2$, CH, O, S, or NH;
Q=a bond or CH=CH;
n=0, 1, or 2; and
Z=H or halogen;
or a pharmaceutically acceptable salt thereof.

3. A compound of claim 1 having the formula

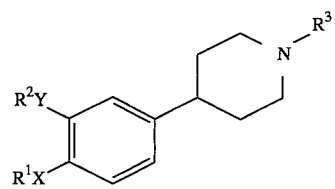

where:
$R^1$=$CH_3$;
$R^2$=$nC_4H_9$,

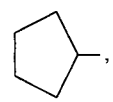

or when Y is CH, $R^2$ is

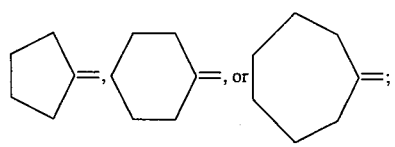

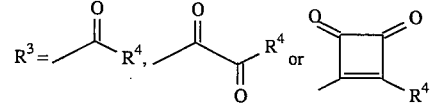

$R^4$=$OR^5$, $NHR^5$ or NHOH;
$R^5$=H, $C_1$–$C_3$ alkyl or

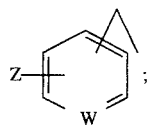

W=N or CH;
X=CH$_2$ or O;
Y=CH$_2$, CH, or O and
Z=H or halogen;
or a pharmaceutically acceptable salt thereof.

4. A compound according to claim 1 selected from
4-(3-cyclopentyloxy-4-methoxyphenyl)-piperidine-1-carboxylic acid amide,
4-(3-cyclopentyloxy-4-methoxyphenyl)-piperidine-1-carboxylic acid methyl ester,
4-[3-(cyclopentyloxy)-4-methoxyphenyl]-N-(2-pyridinemethyl)- 1-piperidinecarboxamide, and
4-(3-cyclopentylmethyl-4-methoxyphenyl-piperidine-1-carboxylic acid amide.

5. A compound according to claim 1 selected from:
2-[4-(3-cyclopentyloxy-4-methoxyphenyl)piperidine-1-yl]-2-oxo-acetic acid ethyl ester,
2-[4-(3-cyclopentyloxy-4-methoxyphenyl)piperidine-1-yl]-2-oxo-acetic acid,
2-[4-(3-cyclopentyloxy-4-methoxyphenyl)piperidine-1-yl]-2-oxo-acetamide,
2-[4-(3-cyclopentyloxy-4-methoxyphenyl)piperidine-1-yl]-2-oxo-N-pyridin-3-ylmethyl acetamide,
2-[4-(3-cyclopentyloxy-4-methoxyphenyl)piperidine-1-yl]-N-hydroxy-2-oxo-acetamide,
2-[4-(3-cyclopentylmethyl-4-methoxyphenyl)piperidine-1-yl]-N-hydroxy-2-oxo-acetamide,
2-[4-(3-cyclopentylmethyl-4-methoxyphenyl)piperidine-1-yl]-2-oxo-acetamide,
2-[4-(3-cyclopentylidenemethyl-4-methoxy-phenyl)-piperidin- 1-yl]-oxo-acetic acid ethyl ester,
2-[4-(3-cyclopentylidenemethyl-4-methoxy-phenyl)-piperidin- 1-yl]-N-hydroxy-2-oxo-acetamide,
[4-(3-cyclopentylidenemethyl-4-methoxy-phenyl)-piperidin- 1-yl]-oxo-acetic acid sodium salt hydrate,
2-[4-(3-cycloheptylidenemethyl-4-methoxy-phenyl)-piperidin- 1-yl]-oxo-acetamide,
2-[4-(3-cycloheptylidenemethyl-4-methoxy-phenyl)-piperidin- 1-yl]-oxo-acetic acid ethyl ester,
2-[4-(3-cycloheptylidenemethyl-4-methoxy-phenyl)-piperidin- 1-yl]-N-hydroxy-2-oxo-acetamide, and
2-[4-(3-cycloheptylidenemethyl-4-methoxy-phenyl)-piperidin- 1-yl]-oxo-acetic acid.

6. A compound according to claim 1 selected from:
3-[4-(3-cyclopentyloxy-4-methoxyphenyl)piperidin-1-yl]-3-oxo-propionic acid methyl ester,
3-[4-(3-cyclopentyloxy-4-methoxyphenyl)piperidin-1-yl]-3-oxo-propionic acid,
3-[4-(3-cyclopentyloxy-4-methoxyphenyl)piperidin-1-yl]-3-oxo-propionamide,
3-[4-(3-cyclopentyloxy-4-methoxyphenyl)piperidin-1-yl]-2-(hydroxyimino)-3-oxo-propionic acid methyl ester,
3-[4-(3-cyclopentyloxy-4-methoxyphenyl)piperidin-1-yl]-2-(hydroxyimino)-3-oxo-propionamide,
(E)-3-[[4-(3-cyclopentyloxy-4-methoxyphenyl)piperidin-1-yl]-2-(hydroxyimino)-3-oxo-propionamide, and
3-[4-(3-cyclopentyloxy-4-methoxyphenyl)piperidin-1-yl]-2-(hydroxyimino)-3-oxo-propionic acid.

7. A compound according to claim 1 selected from:
3-[4-(3-cyclopentyloxy-4-methoxy-phenyl)-piperidin-1-yl]-4-isopropoxy-cyclobut-3-ene-1,2-dione,
3-[4-(3-cyclopentyloxy-4-methoxy-phenyl)-piperidin-1-yl]-4-hydroxy-cyclobut-3-ene-1,2-dione, and
3-[4-(3-cyclopentyloxy-4-methoxy-phenyl)-piperidin-1-yl]-4-hydroxyamino-cyclobut-3-ene-1,2-dione.

8. A pharmaceutical composition for treating asthma in mammals which comprises a pharmaceutically acceptable carrier and a therapeutically effective amount of a compound of the formula:

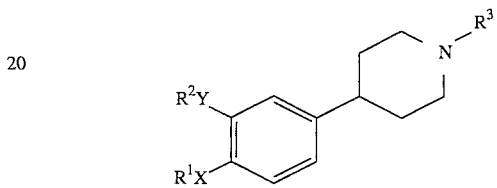

where:
R$^1$=H, C$_1$–C$_6$ alkyl;
R$^2$=C$_3$–C$_7$ alkyl, C$_3$–C$_7$ cycloalkyl or C$_4$–C$_8$ cycloalkylidene when Y is CH;

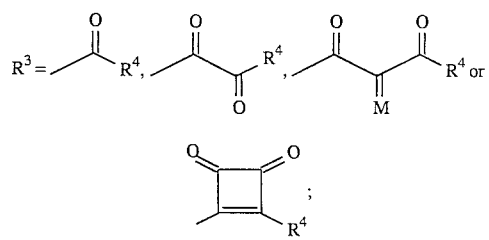

R$^4$=H, OR$^5$, NHR$^5$, NHOH, NHNH$_2$ or

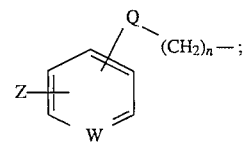

R$^5$=H, C$_1$–C$_6$ alkyl, C$_3$–C$_8$ cycloalkyl, aryl, substituted aryl, aralkyl, substituted aralkyl or

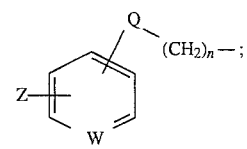

W=N or CH;
X=CH$_2$, O, S, or NH;
Y=CH$_2$, CH, O, S, or NH;
Q=a bond or CH=CH;
n=0, 1, 2, 3 or 4;

M=O, NOH or H$_2$;

Z=H or halogen;

or a pharmaceutically acceptable salt thereof.

9. A method of treating asthma in mammals which comprises administration to the mammal in need thereof of a therapeutically effective amount of a compound of the formula:

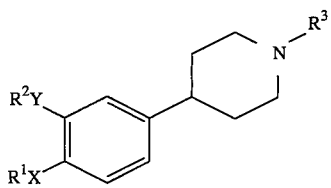

where:

R$^1$=H, C$_1$–C$_6$ alkyl;

R$^2$=C$_3$–C$_7$ alkyl, C$_3$–C$_7$ cycloalkyl or C$_4$–C$_8$ cycloalkyldiene when Y is CH;

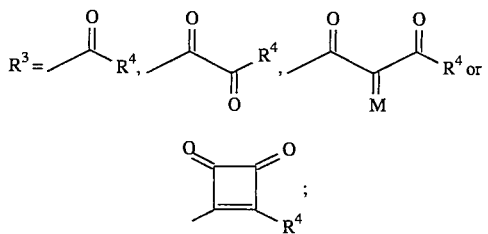

R$^4$=H, OR$^5$, NHR$^5$, NHOH, NHNH$_2$ or

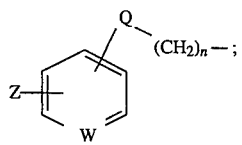

R$^5$=H, C$_1$–C$_6$ alkyl, C$_3$–C$_8$cycloalkyl, aryl substituted aryl, aralkyl, substituted aralkyl or

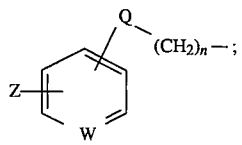

W=N or CH;

X=CH$_2$, O, S, or NH;

Y=CH$_2$, CH, O, S, or NH;

Q=a bond or CH=CH;

n=0,1, 2, 3, or 4;

M=O, NOH or H$_2$;

Z=H or halogen;

or a pharmaceutically acceptable salt thereof.

10. The method according to claim 9 wherein the compound used is selected from:

4-(3-cyclopentyloxy-4-methoxyphenyl)piperidine-1-carboxylic acid amide, 4-(3-cyclopentyloxy-4-methoxyphenyl)piperidine-1-carboxylic acid methyl ester, 4-(3-cyclopentyloxy-4-methoxyphenyl]-1-[(E)-1-oxo-3-phenyl-2-propenyl]piperidine, 4-(3-cyclopentyloxy-4-methoxyphenyl]-1-[(E)-1-oxo-3-(3-pyridinyl-2-propenyl]piperidine, 4-[3-cyclopentyloxy-4-methoxyphenyl]-N-(2-pyridinemethyl)- 1-piperidinecarboxamide, and 4-(3-cyclopentyloxy-4-methoxyphenyl]-piperidine-1-carboxylic acid amide.

11. The method according to claim 9 wherein the compound used is selected from:

2-[4-(3-cyclopentyloxy-4-methoxyphenyl)piperidine-1-yl]- 2-oxo-acetic acid ethyl ester, 2-[4-(3-cyclopentyloxy-4-methoxyphenyl)piperidin-1-yl]- 2-oxo-acetic acid, 2-[4-(3-cyclopentyloxy-4-methoxyphenyl)piperidin-1-yl]- 2-oxo-acetamide, 2-[4-(3-cyclopentyloxy-4-methoxyphenyl)piperidin-1-yl]- 2-oxo-N-pyridin-3-ylmethyl acetamide, 2-[4-(3-cyclopentyloxy-4-methoxyphenyl)piperidin-1-yl] -N-hydroxy- 2-oxo-acetamide, 2-[4-(3-cyclopentymethyl-4-methoxyphenyl)piperidin-1-yl]-N-hydroxy- 2-oxo-acetamide, 2-[4-(3-cyclopentymethyl-4-methoxyphenyl)piperidin-1-yl]-2-oxo-acetamide, 2-[4-(3-cyclopentylidenemethyl-4-methoxy-phenyl)-piperidin-1-yl]-oxo-acetic acid ethyl ester, 2-[4-(3-cyclopentylidenemethyl-4-methoxy-phenyl)-piperidin-1-yl]-N-hydroxy- 2-oxo-acetamide,

[4-(3-cyclopentylidenemethyl-4-methoxy-phenyl)-piperidin-1-yl]-oxo-acetic acid sodium salt hydrate, 2-[4-(3-cyclopentylidenemethyl-4-methoxy-phenyl)-piperidin-1-yl]-2-oxo-acetamide, 2-[4-(3-cycloheptylidenemethyl-4-methoxy-phenyl)-piperidin-1-yl]-oxo-acetic acid ethyl ester, 2-[4-(3-cycloheptylidenemethyl-4-methoxy-phenyl)-piperidin-1-yl]-N-hydroxy- 2-oxo-acetamide, and 2-[4-(3-cycloheptylidenemethyl-4-methoxy-phenyl)-piperidin-1-yl]-oxo-acetic acid.

12. The method according to claim 9 wherein the compound used is selected from:

3-[4-(3-cyclopentyloxy-4-methoxy-phenyl)piperidin-1-yl]-3-oxo-propionic acid methyl ester, 3-[4-(3-cyclopentyloxy-4-methoxy-phenyl)piperidin-1-yl]-3-oxo-propionic acid, 3-[4-(3-cyclopentyloxy-4-methoxy-phenyl)piperidin-1-yl]-3-oxo-propionamide, 3-[4-(3-cyclopentyloxy-4-methoxyphenyl)piperidin-1-yl]- 2-(hydroxyimino)-3-oxo-propionic acid methyl ester, 3-[4-(3-cyclopentyloxy-4-methoxyphenyl)piperidin-1-yl]- 2-(hydroxyimino)-3-oxo-propionamide, (E)-3-[[4-(3-cyclopentyloxy-4-methoxyphenyl)piperidin-1-yl]-2-(hydroxyimino)-3-oxo-propionamide, and 3-[4-(3-cyclopentylmethyl-4-methoxyphenyl)piperidin-1-yl]-2-(hydroxyimino)-3-oxo-propionic acid.

13. The method according to claim 9 wherein the compound used is selected from:

3-[4-(3-cyclopentyloxy-4-methoxy-phenyl)-piperidin-1-yl]-4-isoproxycyclobut-3-ene-1,2-dione, 3-[4-(3-cyclopentyloxy-4-methoxy-phenyl)-piperidin-1-yl]-4-hydroxy-cyclobut-3-ene-1,2-dione, and 3-[4-(3-cyclopentyloxy-4-methoxy-phenyl)-piperidin-1-yl]-4-hydroxyamino-cyclobut-3-ene-1,2-dione.

* * * * *